US007049331B2

(12) United States Patent
Eisinger et al.

(10) Patent No.: US 7,049,331 B2
(45) Date of Patent: *May 23, 2006

(54) 1,2,4-THIADIAZOLE DERIVATIVES AS MELANOCORTIN RECEPTOR MODULATORS

(75) Inventors: Magdalena Eisinger, Demarest, NJ (US); Louis J. Fitzpatrick, Souderton, PA (US); Daniel H. Lee, Sudbury, MA (US); Kevin Pan, Phoenixville, PA (US); Carlos Plata-Salaman, Ambler, PA (US); Allen B. Reitz, Lansdale, PA (US); Virginia L. Smith-Swintosky, Hatfield, PA (US); Boyu Zhao, Lansdale, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/287,095

(22) Filed: Nov. 4, 2002

(65) Prior Publication Data

US 2003/0176425 A1   Sep. 18, 2003

Related U.S. Application Data

(60) Provisional application No. 60/337,927, filed on Nov. 8, 2001.

(51) Int. Cl.
*A61K 31/433* (2006.01)
*C07D 285/08* (2006.01)
(52) U.S. Cl. .................. 514/361; 548/125; 548/128
(58) Field of Classification Search ............ 548/190, 548/93, 128, 125; 514/370, 361
See application file for complete search history.

(56) References Cited

U.S. PATENT DOCUMENTS

| 6,294,534 B1 | 9/2001 | Nargund et al. |
| 6,410,548 B1 | 6/2002 | Nargund et al. |

FOREIGN PATENT DOCUMENTS

| DE | 131.373 | 6/1978 |
| JP | 60-11481 | 1/1985 |
| JP | 2-173165 | 7/1990 |
| WO | WO 99/55679 A1 | 11/1999 |
| WO | WO 99/64002 A1 | 12/1999 |
| WO | WO 00/24725 A1 | 5/2000 |
| WO | WO 01/55107 A | 8/2001 |

OTHER PUBLICATIONS

Chetia et al (1985): STN International CAPLUS database (Columbus, Ohio), Accession No. 1985:471257.*
Abraham, W. et al., "Formamidinyl Isothiocyanates-III Addition Nucleophilic Partners to Formamidinoyl Isothyiocyantes", Tetrahedron 29, 1973, pp. 699-705 (English Translation).
PCT International Search Report, dated Jan. 1, 2003, for PCT Appl. No. PCT/US02/35340.
Abraham, W. et al., "Formamidinoylisothiocyanate—III, Additional Nucleophiler Partner and Formamidinoylisothiocyanate", Tetrahedron, vol. 29, No. 5, pp. 699-705, Mar. 1973, XP002228008.
Barbier, B et al; "Crystal Structure of 2-benzyl-3-phenyl-5-phenylimino-$\Delta^3$-1,2,4-thiadiaoline, $C_{21}H_{17}N_3S$"; Z. Kristallogr.NCS (1998). pp 741-742, vol. 213.
Barnikow, Gunter et al; Regarding the oxidative cyclization of imidoyl-thioureas ; Z. Chem., (1972), pp. 130, vol. 12-No. 4.
Chetia, J.P. et al; "One-Pot Synthesis of 2-Aryl-3-phenyl(benzyl)-5-phenylimino-$\Delta^4$-1,2,4-thiadiazolines using *N*-Chlorosuccinimide"; Synthesis Communications. Jan. 1985. pp 83-84.
Fawzi, Ahmad B. et al; "SCH-202676 An Allosteric Modulator of Both Agonist and Antagonist Binding to G Protein-Coupled Receptors"; Molecular Pharmacology, (2001). pp 30-37; vol. 59- No. 1.
Goerdeler, Joachim et al; "Herstellung von Acylheterocumulenen aus fünfgliedrigen Ringen mit Hilfe von Phosphinen" Chem. Ber. (1974). pp. 502-507; vol. 107.
Goerdeler, Joachim et al; "Herstellung von (*N*-Alkylbenzimidoyl)- und (*N*-Arylbenzimidoyl)carbodiimiden; ihre Umlagerung zu Aminochinazolinen und Dihydro-1,3,5-triazinen"; Chem. Ber. (1986), pp. 3737-3748, vol. 119.
Goerdeler, Joachim et al; "Reaktion von Heterocumulenen mit 5-Alhoxy-3-phenylimino3*H*-1,2,4-dithiazol", Chem. Ber. (1976), pp. 848-854, vol. 109.
Goerdeler, Joachim et al; "Reaktionen von 5-limino-$\Delta^3$-1,2,4-thiadiazolinen mit Heterocumulenen (Präparative Gesichtspunkte)": Chem. Ber. (1979): pp. 517-531, vol. 112.

(Continued)

*Primary Examiner*—Golam M. M. Shameem
(74) *Attorney, Agent, or Firm*—Mary Appollina; Hal Brent Woodrow

(57) ABSTRACT

The present invention is directed to novel 1,2,4-thiadiazole derivatives useful as agonists or antagonists of the melanocortin receptor. More particularly, the compounds of the present invention are useful for the treatment of metabolic, CNS and dermatological disorders such as obesity, impaired oral glucose tolerance, elevated blood glucose levels, type II diabetes, Syndrome X, diabetic retinopathy, spinal cord injury, nerve injury, acute neurodegenerative disorders, chronic neurodegenerative disorders, plexopathies, male erectile dysfunction, dry eyes, acne, dry skin, aged skin, seborrheic dermatitis, rosacea, excessive ear wax, meibomian gland disorder, pseudofolliculitis, yeast infections, dandruff, hidradenitis suppurativa, ocular rosacea and eccrine gland disorder.

19 Claims, No Drawings

OTHER PUBLICATIONS

Goerdeler, Joachim et al; "Uber die Zerfallsprodukte von lmino-$\Delta^3$-1,2,4-thiadiazolinen"; Chem. Ber. (1979). pp. 1288-1296 vol. 112.

Hagiwara, Kenji et al; Synthesis and Fungicidal Activity of $\Delta^3$-1,2,4-Thiadiazolines: Journal of Pesticide Science. (1992) pp. 251-259, vol. 17.

L'Abbe, Gerrit et al: "5-lmino-$\Delta^3$-1,2,4-thiadiazoline Derivatives with a Linear N-S . . . O Grouping Synthesis and Crystal Structures", J Heterocyclic Chem., Nov. 1981, pp. 1309-1317, vol. 18.

Liebscher, Jürgen et al; "Oxidation-assisted synthesis of N-imidoyl-guanidines from N-imidoyl-thioureas"; Z. Chem., (1985). pp. 362-363, vol. 25, No. 10.

Nair, M.D. et al; "Oxidation of N-Phenyl-N-phenylthiocarbamoylbenzamidines with Sulphuryl Chloride & Bromine"; Indian Journal of Chemistry, May 1980, pp. 335-337, vol. 19B.

Neidlein, R. et al; " Zum Reaktionsverhalten Von N-Acyl-S-Chlorisothiocarbamoylchloriden"; Tetrahedron, (1971), pp 4117-4124, vol. 27.

Wikberg, Jarl E.S.; "Melanocortin receptors: new opportunities in drug recovery"; Exp. Opin. Ther. Patents; (2001), pp. 61-76, vol. 11-No. 1.

Zyabrev, V.S. et al; "Chlorination of Imidoyl Isothiocyanates": Ukrainskii Khimcheskii Zhurnal; (1995), pp. 55-61, vol. 61, No. 5.

S. Rajappa et al., "A General Synthesis of Thiazoles, Part 3, Comparative Evaluation of Different Functionalised Thioureas as Precursors," J.C.S. Perkin I, May 1978, pp. 1762-1764.

J. Goerdeler et al, Chem. Ber. 112, pp. 1288-1296 (1979) with English-language translation.

Z. Chem. vol. 25 (1985) No. 10, pp. 362-363 with English-language translation.

J. Goerdeler et al., Chem. Ber. 101, 3475-3490 (1968) with English-language abstract.

* cited by examiner

1,2,4-THIADIAZOLE DERIVATIVES AS MELANOCORTIN RECEPTOR MODULATORS

CROSS REFERENCE TO RELATED APPLICATION

This application claims the benefit of U.S. Provisional Application No. 60/337,927, filed on Nov. 8, 2001, which is incorporated by reference herein in its entirety.

FIELD OF THE INVENTION

The present invention provides novel 1,2,4-thiadiazole derivatives useful for the treatment of a disorder mediated by a melanocortin receptor. More particularly, the compounds of the present invention are useful for the treatment of metabolic, CNS and dermatologic disorders such as obesity, impaired oral glucose tolerance, elevated blood glucose levels, type II diabetes, Syndrome X, diabetic retinopathy, acute neurodegenerative disorders, chronic neurodegenerative disorders, plexopathies, male erectile dysfunction, dry eyes, acne, dry skin, aged skin, seborrheic dermatitis, rosacea, excessive ear wax, meibomian gland disorder, pseudofolliculitis, yeast infections, dandruff, hiradenitis suppurativa, ocular rosacea and eccrine gland disorder.

BACKGROUND OF THE INVENTION

Melanocortins are neuropeptides that arise from pro-opiomelanocortin (POMC), which is most prevalently expressed in the arcuate nucleus of the hypothalamus, pituitary lobes, and the nucleus tractus solarius of the brainstem. [Gantz, I., et al., *Molecular Cloning, Expression, and Gene Localization of a Fourth Melanocortin Receptor*, J. Biolog. Chem., 1993, 268, 15174–15179.] These peptides include ACTH, α-MSH, β-MSH, $\gamma_{1-3}$-MSH, and synthetic analogue NDP-αMSH (Wikberg, J E S, *Melanocortin receptors: new opportunities in drug discovery*, Exp. Opin. Ther. Patents, 2000, 11(1), 61–76).

These peptides bind to five types of melanocortin receptors (MC1-MC5), which are G-protein coupled receptors that all positively modulate adenylate cyclase. The MC4 and MC5 receptors are widely distributed in the brain and spinal cord, whereas the MC3 receptor is located mainly in the hypothalamus. [Gantz, I., et al., supra.] The MC4 receptor is selectively activated by αMSH and can induce neurite outgrowth in Neuro 2A cells. (Adan R. A. H, et al., Molecular Brian Research, 1996, 36, pp 37–44; Mountjoy, K. G., Mortud, M. T., Low, M. J., Simerly, R. B. and Cone, R. D., Mol. Endocrinol., 1994, 8, pp 1298–1308). ACHT is a less potent activator of the MC4 receptor than αMSH. (Adan, R. A. H., Cone, R. D., Burbach, J. P. H. and Gispen, W. H., mol. pharmacol., 1994, 46, pp 1182–1190). The MC5 receptor is activated, in order of degree, by NDP ≈α-MSH>ACHT (1–24)≧α MSH ACHT (1–39)=βMSH>>γMSH (*The Melanocortin Receptors*, Cone, R. D., Editor, Human Press Inc., Totowa, N.J., 2000, Chen, W., pp449–472)

In whole animals, studies in the rat sciatic nerve crush model have demonstrated that α-MSH increases neurite outgrowth and, as the most potent of the ACTH derived peptides, it significantly promotes nerve terminal branching, endplate area, and perimeter. [Bijlsma, W. A., et al., *The Enhanced Recovery of Sensorimotor Function in Rats is Related to the Melantropic Moiety of ACTH/MSH Neuropeptides*, Eur. J. Pharmacol, 1983, 92, 231–236; Van der Neut. R., et al., *Stimulation by Melanocortins of Neurite Outgrowth from Spinal and Sensory Neurons In Vitro*, Peptides, 1992, 13, 1109–1115; Van Der Zee, C. E. E. M., et al., α-MSH and Org 2766 in *Peripheral Nerve Regeneration: Different Route of Delivery*, Eur. J. Pharmacol., 1988, 147, 351–357; Strand, F. L., et al., *Melanocortins as Factors in Somatic Neuromuscular Growth and Regrowth*, Pharmac. Ther., 1994, 62, 1–27]. Furthermore, recovery of motor function after nerve injury is shortened by application of α-MSH and other melanocortins. [Strand, F. L., et al., supra]

Mice in which the MC4 receptor is rendered inactive by gene targeting become obese, suggesting that the MC4 receptor is involved in feeding. [Huszar, D., et al., *Targeted Disruption of the Melanocortin4 Receptor Results in Mice*, Cell, 1997, 88, 131–141] This is substantiated by a report that various MC4 peptide agonists inhibit feeding behavior in agouti mice. [Fan, W., et al., *Role of Melanocortingenic Neurons in Feeding and the Agouti Obesity Syndrome*, Nature, 1997, 385, 165–168]. α-MSH induces grooming behavior in rats, but the significance of this is not clear and may not be mediated via the MC4 receptor. [Adan, R. A. H., et al., *Differential Effects of Melanocortin Peptides on Neural Melanocortin Receptors*, Molecular Pharmacology, 1994, 46, 1182–1190].

The melanocortins αMSH and ACTH are also known for their ability to stimulate pigmentation and adrenal glucocorticoid secretion, respectively. The role of melanocortins, particularly αMSH, in the regulation of sebaceous gland activity (an exocrine gland with holocrine type of secretion) was shown originally in rats. More particularly, the studies showed that removal of the intermediate lobe of the pituitary (which produces the POMC peptides) resulted in decreased sebaceous lipid production, with complete restoration to normal levels after replacement therapy with αMSH (Thody, A. J. and Shuster, Nature, 237, 346–347, 1972). In a study of rats following total hypophysectomy, treatment with αMSH resulted in an increase of sebum production, although full restoration of sebum production was achieved only after treatment with a combination of αMSH and testosterone (Thody, A. J., Shuster, S., J. Endocr. 64, 503–510, 1975; Ebling, F. J., Ebling, E., Randall, V. and Skinner, J., *J. Endocr.* 66, 407–412, 1975). Knock-out mice where the MC5 receptor was deleted were observed to display a severe defect in water repulsion and thermo-regulation, due to decreased production of sebaceous lipids (Chen, W. Kelly, M. A., Opitz-Araya, X., Thomas, R. E., Low, M. J., and Cone, R., Cell, 91, 788–798, 1997).

The MC5 receptor is known to be expressed in human sebaceous glands, and may be involved in the regulation of human sebaceous lipid synthesis. Human MC5-R has been cloned and characterized (Chhajlani, V., Muceniece, R., Wikberg, J E S., Biochem. Biophys. Res. Commun. 195, 866–873, 1993). Moreover, presence of MC5-R m RNA in human sebaceous glands has been shown by RT-PCR and the protein was detected by immunohistochemistry and Western blot analysis (Thiboutot, D., Sivarajah, Gililand, K., Cong, Z. and Clawson, G., *J. Invest. Dermatol.* 115(4), 614–619, 2000).

Human sebum differs in its composition from other mammals. The main lipids in human sebum are triglycerides, wax esters and squalene (Greene, R. S., Downing, D. T., Poci, P. E., Strauss, J. S., *JID* 54, 240–247, 1970). Squalene, for instance is not found in many mammals with the exception of otter and beaver. Triglyceride, which is a major component of human sebum is poorly represented in other species and in many (e.g. chimpanzee) appears to be totally absent (Thody, A. J., Shuster, S., *Physiolog. Rev.* 69, 383–415, 1989). Moreover melanocortins can have different effects on cells from different species. For example both αMSH (EC₅₀=3.7 nM) and ACTH (EC₅₀=16.4 nM) are potent lipolytic agents for rabbit adipocytes, whereas in the rat only ACTH (EC₅₀=1.34 nM) has potent lipolytic activity (Ramachadran, J., Lee, V., 428, 339–346, 1987; Richter, W. O., Schwandt, P., *Neuropeptides* 9, 59–74, 1987). Despite lipolytic activity in rodents and rabbits, ACTH has very little effect on lipolysis in isolated human and non-human primate adipocytes, even at concentrations as high as 1 μM (Ng, T. B. *Comparative Biochem.* 97, 441–446, 1990). Thus defining the role of melanocortins and their receptors in animal sebaceous model systems is not necessarily predictive of their role in a human sebaceous lipid regulation.

Recently, Basu et. al., in WIPO publication WO99/55679 disclosed isoquinoline derivatives, small molecule non-peptide compounds, which showed low micromolar affinities for the MC1 and MC4 receptors, reduction of dermal inflammation induced by arachidonic acids, and reductions of body weight and food intake.

Nargund et. al., in WIPO publication WO99/64002 disclosed spiropiperidine derivatives as melanocortin receptor agonists, useful for the treatment of diseases and disorders such as obesity, diabetes and sexual dysfunction.

Thus there exist a need for small molecule modulators of the melanocortin receptor, more particularly the melanocortin-3, melanocortin-4 and/or the melanocortin-5 receptors.

SUMMARY OF THE INVENTION

The present invention is directed to compounds of the general formula (II)

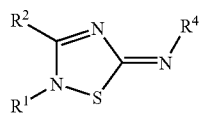

(II)

wherein $R^1$ is selected from the group consisting of heteroaryl, heteroaryl-alkyl, heterocycloalkyl, heterocycloalkyl-alkyl, cycloalkyl, cycloalkyl-alkyl, substituted aryl and substituted aralkyl; ($R^1$ is not unsubstituted aryl or unsubstituted aralkyl);

wherein the heteroaryl, heteroaryl-alkyl, heterocycloalkyl, heterocycloalkyl-alkyl, cycloalkyl or cycloalkyl-alkyl group is optionally substituted with one or more substituents independently selected from halogen, hydroxy, alkyl, alkoxy; halogenated alkyl, halogenated alkoxy, amino, alkylamino or di(alkyl)amino;

wherein the aryl or aralkyl group is substituted with one or more substituents independently selected from halogen, hydroxy, alkyl, alkoxy; halogenated alkyl, halogenated alkoxy, amino, alkylamino or di(alkyl)amino;

$R^2$ is selected from the group consisting of heteroaryl, heteroaryl-alkyl, heterocycloalkyl, heterocycloalkyl-alkyl, cycloalkyl, cycloalkyl-alkyl, substituted aryl and substituted aralkyl; ($R^2$ is not unsubstituted aryl or unsubstitutedd aralkyl);

wherein the heteroaryl, heteroaryl-alkyl, heterocycloalkyl, heterocycloalkyl-alkyl, cycloalkyl or cycloalkyl-alkyl group is optionally substituted with one or more substituents independently selected from halogen, hydroxy, alkyl, alkoxy; halogenated alkyl, halogenated alkoxy, amino, alkylamino or di(alkyl)amino;

wherein the aryl or aralkyl group is substituted with one or more substituents independently selected from halogen, hydroxy, alkyl, alkoxy; halogenated alkyl, halogenated alkoxy, amino, alkylamino or di(alkyl)amino;

$R^4$ is selected from the group consisting of aryl, aralkyl, heteroaryl, heterocycloalkyl, and cycloalkyl-alkyl; wherein the aryl, aralkyl, heteroaryl, heterocycloalkyl or cycloalkyl-alkyl group is optionally substituted with one or more substituents independently selected from halogen, hydroxy, alkyl, alkoxy; halogenated alkyl, halogenated alkoxy, amino, alkylamino or di(alkyl)amino;

provided that when $R^1$ is aryl substituted with one halogen and $R^4$ is aryl substituted with one halogen, then $R^2$ is not morpholinyl;

and pharmaceutically acceptable salts thereof.

The present invention is further directed to compounds of the general formula (II)

(II)

wherein $R^1$ is selected from the group consisting of heteroaryl, heteroaryl-alkyl, heterocycloalkyl, heterocycloalkyl-alkyl, cycloalkyl, cycloalkyl-alkyl, substituted aryl and substituted aralkyl; ($R^1$ is not unsubstituted aryl or unsubstituted aralkyl);

wherein the heteroaryl, heteroaryl-alkyl, heterocycloalkyl, heterocycloalkyl-alkyl, cycloalkyl or cycloalkyl-alkyl group is optionally substituted with one or more substituents independently selected from halogen, hydroxy, alkyl, alkoxy; halogenated alkyl, halogenated alkoxy, amino, alkylamino or di(alkyl)amino;

wherein the aryl or aralkyl group is substituted with one or more substituents independently selected from halogen, hydroxy, alkyl, alkoxy; halogenated alkyl, halogenated alkoxy, amino, alkylamino or di(alkyl)amino;

$R^2$ is selected from the group consisting of aryl, aralkyl, heteroaryl, heteroaryl-alkyl, heterocycloalkyl, heterocycloalkyl-alkyl, cycloalkyl, cycloalkyl-alkyl, substituted aryl and substituted aralkyl;

wherein the aryl, aralkyl, heteroaryl, heteroaryl-alkyl, heterocycloalkyl, heterocycloalkyl-alkyl, cycloalkyl or cycloalkyl-alkyl group is optionally substituted with one or more substituents independently selected from halogen, hydroxy, alkyl, alkoxy; halogenated alkyl, halogenated alkoxy, amino, alkylamino or di(alkyl)amino;

$R^4$ is selected from the group consisting of heteroaryl, heterocycloalkyl, cycloalkyl-alkyl, substituted aryl and substituted aralkyl; ($R^4$ is not unsubstituted aryl or unsubstttuted aralkyl);

wherein the heteroaryl, heterocycloalkyl or cycloalkyl-alkyl group is optionally substituted with one or more substituents independently selected from halogen, hydroxy, alkyl, alkoxy; halogenated alkyl, halogenated alkoxy, amino, alkylamino or di(alkyl)amino;

wherein the aryl or aralkyl group is substituted with one or more substituents independently selected from halogen, hydroxy, alkyl, alkoxy; halogenated alkyl, halogenated alkoxy, amino, alkylamino or di(alkyl)amino;

provided that when R¹ is aryl substituted with one halogen and R⁴ is aryl substituted with one halogen, then R² is not morpholinyl;

provided further that when R¹ is methylphenyl and R⁴ is methoxyphenyl, then R² is selected from the group consisting of aralkyl, heteroaryl, heteroaryl-alkyl, heterocycloalkyl, heterocycloalkyl-alkyl, cycloalkyl, cycloalkyl-alkyl and substituted aryl;

wherein the aralkyl, heteroaryl, heterocycloalkyl or cycloalkyl group is optionally substituted with one or more substituents independently selected from halogen, hydroxy, alkyl, alkoxy; halogenated alkyl, halogenated alkoxy, amino, alkylamino or di(alkyl)amino;

wherein the aryl group is substituted with one or more substituents independently selected from halogen, hydroxy, alkyl, alkoxy; halogenated alkyl, halogenated alkoxy, amino, alkylamino or di(alkyl)amino;

and pharmaceutically acceptable salts thereof.

The present invention is further directed to a method for treating disorders mediated by a melanocortin receptor comprising administering to a subject in need thereof a therapeutically effective amount of a compound of formula (II)

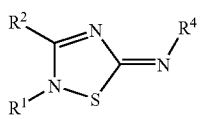

(II)

wherein

R¹ is selected from the group consisting of alkyl, aryl, aralkyl, heteroaryl, heteroaryl-alkyl, heterocycloalkyl, heterocycloalkyl-alkyl, cycloalkyl and cycloalkyl-alkyl; wherein the aryl, aralkyl, heteroaryl, heteroaryl-alkyl, heterocycloalkyl, heterocycloalkyl-alkyl, cycloalkyl or cycloalkyl-alkyl group is optionally substituted with one or more substituents independently selected from halogen, hydroxy, alkyl, alkoxy; halogenated alkyl, halogenated alkoxy, amino, alkylamino or di(alkyl)amino;

R² is selected from the group consisting of alkyl, aryl, aralkyl, heteroaryl, heterocycloalkyl and cycloalkyl-alkyl; wherein the aryl, aralkyl, heteroaryl, heteroaryl-alkyl, heterocycloalkyl, heterocycloalkyl-alkyl, cycloalkyl or cycloalkyl-alkyl group is optionally substituted with one or more substituents independently selected from halogen, hydroxy, alkyl, alkoxy; halogenated alkyl, halogenated alkoxy, amino, alkylamino or di(alkyl)amino;

R⁴ is selected from the group consisting of hydrogen, alkyl, aryl, aralkyl, heteroaryl, heterocycloalkyl, and cycloalkyl-alkyl; wherein the aryl, aralkyl, heteroaryl, heterocycloalkyl or cycloalkyl-alkyl group is optionally substituted with one or more substituents independently selected from halogen, hydroxy, alkyl, alkoxy; halogenated alkyl, halogenated alkoxy, amino, alkylamino or di(alkyl) amino;

and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating disorders mediated by the melanocortin receptor in a subject in need thereof comprising administering to the subject a therapeutically effective amount of any of the compounds or pharmaceutical compositions described above.

An embodiment of the present invention is the use of any of the compounds described herein for the treatment of a disorder selected from the group consisting of metabolic disorders, CNS disorders and dermatological disorders.

An example of the invention is a method for treating a disorder selected from the group consisting of obesity, impaired oral glucose tolerance, elevated blood glucose levels, type II diabetes, Syndrome X, diabetic retinopathy, spinal cord injury, nerve injury, acute neurodegenerative disorders, chronic neurodegenerative disorders, plexopathies, male erectile dysfunction, dry eyes, acne, dry skin, aged skin, seborrheic dermatitis, rosacea, excessive ear wax, meibomian gland disorder, pseudofolliculitis, yeast infections, dandruff, hidradenitis suppurativa, ocular rosacea and eccrine gland disorder in a subject in need thereof comprising administering to the subject a therapeutically effective amount of any of the compounds or pharmaceutical compositions described above.

Another example of the invention is the use of any of the compounds described herein in the preparation of a medicament for treating: (a) obesity, (b) impaired oral glucose tolerance, (c) elevated blood glucose levels, (d) type II diabetes, (e) Syndrome X, (f) diabetic retinopathy, (g) an acute neurodegenerative disorder, (h) a chronic neurodegenerative disorder, (i) a plexopathy, (j) male erectile dysfunction, (k) dry eyes, (i) acne, (m) dry skin, (n) aged skin, (O) seborrheic dermatitis, (p) rosacea, (q) excessive ear wax, (r) meibomian gland disorder, (s) pseudofolliculitis, (t) yeast infections, (u) dandruff, (v) hidradenitis suppurativa, (w) ocular rosacea or (x) eccrine gland disorder, in a subject in need thereof.

DETAILED DESCRIPTION OF THE INVENTION

The present invention is directed to novel substituted 1,2,4-thiadiazole derivatives useful for the treatment of disorders mediated by a melanocortin receptor. More particularly, the present invention is directed to compounds of formula (II)

(II)

wherein R¹, R² and R⁴ are as herein defined, useful as melanocortin receptor agonists or antagonists.

The present invention is further directed to a method of treating a disorder mediated by a melanocortin receptor, preferably a disorder which is susceptible to treatment by agonism or antagonism of a melanocortin receptor. Preferably the melanocortin receptor is selected from the group consisting of the melanocortin-3, melanocortin-4 and melanocortin-5 receptor, more preferably the melanocortin receptor is melanocortin-4 or melanocortin-5.

In an embodiment of the present invention, R¹ is selected from the group consisting of aryl, aralkyl and heteroaryl; wherein the aryl, aralkyl or heteroaryl group is optionally substituted with one or more substituents independently selected from halogen, hydroxy, alkyl, alkoxy; trihalomethyl, trihalomethoxy, amino, alkylamino or di(alkyl)amino. Preferably, $R^1$ is selected from the group consisting of aryl; wherein aryl group is optionally substituted with one or more substituents independently selected from halogen, alkyl and alkoxy. More preferably, $R^1$ is selected from the group consisting of phenyl, 2-chlorophenyl, 4-chlorophenyl, 2-methylphenyl, 4-methylphenyl, 2-methoxyphenyl and 4-methoxyphenyl. Most preferably $R^1$ is 2-methoxyphenyl.

In another embodiment of the present invention $R^1$ is selected from the group consisting of substituted aryl and substituted aralkyl, wherein the aryl or aralkyl is substituted with one to two substituents independently selected from halogen, hydroxy, alkyl, alkoxy, trihalomethyl, trihalomethoxy, amino, alkylamino or di(alkyl)amino. Preferably, $R^1$ is selected from the group consisting of substituted aryl; wherein the aryl group is substituted with a substituent selected from halogen, alkyl or alkoxy. More preferably, $R^1$ is 2-methoxyphenyl.

In yet another embodiment of the present invention, $R^1$ is selected from the group consisting of substituted aryl and substituted aralkyl; wherein the aryl or aralkyl group is substituted with one or more substituents independently selected from halogen, hydroxy, alkyl, alkoxy; halogenated alkyl, halogenated alkoxy, amino, alkylamino or di(alkyl)amino.

In an embodiment of the present invention, $R^2$ is selected from the group consisting of aryl, aralkyl and heteroaryl; wherein the aryl, aralkyl or heteroaryl group is optionally substituted with one or more substituents independently selected from halogen, hydroxy, alkyl, alkoxy; trihalomethyl, trihalomethoxy, amino, alkylamino or di(alkyl)amino. Preferably, $R^2$ is selected from the group consisting of aryl; wherein the aryl group is optionally substituted with one or more substituents independently selected from alkyl and alkoxy. More preferably, $R^2$ is selected from the group consisting of phenyl, 4-methylphenyl, 2-methoxyphenyl and 4-methoxyphenyl. Most preferably, $R^2$ is selected from the group consisting of phenyl and 2-methoxyphenyl.

In another embodiment of the present invention $R^2$ is selected from the group consisting of substituted aryl and substituted aralkyl, wherein the aryl or aralkyl is substituted with one to two substituents independently selected form halogen, hydroxy, alkyl, alkoxy, trihalomethyl, trihalomethoxy, amino, alkylamino or di(alkyl)amino. Preferably, $R^2$ is selected from the group consisting of substituted aryl; wherein the aryl group is substituted with a substituent selected from alkyl or alkoxy. More preferably, $R^2$ is 2-methoxyphenyl.

In yet another embodiment of the present invention, $R^2$ is selected from the group consisting of aryl and aralkyl; wherein the aryl or aralkyl group is optionally substituted with one or more substituents independently selected from halogen, hydroxy, alkyl, alkoxy; halogenated alkyl, halogenated alkoxy, amino, alkylamino or di(alkyl)amino.

In an embodiment of the present invention, $R^4$ is selected from the group consisting of aryl, aralkyl and heteroaryl; wherein the aryl, aralkyl or heteroaryl group is optionally substituted with one or more substituents independently selected from halogen, hydroxy, alkyl, alkoxy; trihalomethyl, trihalomethoxy, amino, alkylamino or di(alkyl)amino. Preferably, $R^4$ is selected from the group consisting of aryl, aralkyl, and heteroaryl; wherein the aryl or aralkyl group is optionally substituted with one or more substituents independently selected from halogen, alkyl and alkoxy. More preferably, $R^4$ is selected from the group consisting of phenyl, 2-chlorophenyl, 4-chlorophenyl, 4-bromophenyl, 2-methylphenyl, 4-methylphenyl, 2-methoxyphenyl, 4-methoxyphenyl, benzyl, 2-chlorobenzyl, 4-chlorobenzyl, 2-methylbenzyl, 4-methylbenzyl, 2-methoxybenzyl, 4-methoxybenzyl, 2,6-difluorophenyl, 3,5-difluorophenyl, 2-chloro-6-methylphenyl and 3-pridyl. Most preferably, $R^4$ is selected from the group consisting of phenyl, 2-methylphenyl, 4-methylphenyl, 2-methoxyphenyl and 4-methoxyphenyl.

In another embodiment of the present invention $R^4$ is selected from the group consisting of aryl, aralkyl or heteroaryl; wherein the aryl, aralkyl or heteroaryl group is optionally substituted with one or more substituents independently selected from halogen, hydroxy, alkyl, alkoxy, trihalomethyl, trihalomethoxy, amino, alkylamino, di(alkyl) amino. Preferably, $R^4$ is selected from the group consisting of aryl and substituted aryl; wherein the substituents on the aryl are one to two independently selected halogen, alkyl or alkoxy. More preferably, $R^4$ is selected from the group consisting of phenyl, 4-methoxyphenyl, 2,6-difluorophenyl, 2-chloro-6-methylphenyl and 3,5-difluorophenyl.

In yet another embodiment of the present invention, $R^4$ is selected from the group consisting of substituted aryl and substituted aralkyl; wherein the aryl or aralkyl group is substituted with one or more substituents independently selected from halogen, hydroxy, alkyl, alkoxy; halogenated alkyl, halogenated alkoxy, amino, alkylamino or di(alkyl) amino.

As used herein, unless otherwise note, the term "disorders mediated by a melanocortin receptor" include, but are not limited to, obesity, impaired oral glucose tolerance, elevated blood glucose levels, type II diabetes, Syndrome X, diabetic retinopathy, acute neurodegenerative disorders, chronic neurodegenerative disorders, plexopathies, male erectile dysfunction, dry eyes, acne, dry skin, aged skin, seborrheic dermatitis, rosacea, excessive ear wax, meibomian gland disorder, pseudofolliculitis, yeast infections, dandruff, hidradenitis suppurativa, ocular rosacea and eccrine gland disorder.

As used herein, unless otherwise noted, the term "metabolic disorders" include, but are not limited to, obesity, impaired oral glucose tolerance, elevated blood glucose levels, type II diabetes and Syndrome X.

As used herein, unless otherwise noted, the term "CNS disorders" include, but are not limited to, diabetic retinopathy, acute neurodegenerative disorders, chronic neurodegenerative disorders and plexopathies.

As used herein, unless otherwise noted, the term "dermatological disorders" include, but are not limited to, dry eyes, acne, dry skin, aged skin, seborrheic dermatitis, rosacea, excessive ear wax, meibomian gland disorder, pseudofolliculitis, yeast infections, dandruff, hidradenitis suppurativa, ocular rosacea and eccrine gland disorder.

As used herein, acute neurodegenerative disorders include various types of acute neurodegenerative disorders associated with neuronal cell death or compromise including cerebrovascular insufficiency, focal or diffuse brain trauma, diffuse brain damage, and spinal cord injury, that is, cerebral ischemia or infarction including embolic occlusion and thrombotic occlusion, reperfusion following acute ischemia, perinatal hypoxic-ischemic injury, cardiac arrest, as well as intracranial hemorrhage of any type (including, but not limited to, epidural, subdural, subarachnoid and intracerebral), and intracranial and intravertebral lesions (including, but not limited to, contusion, penetration, shear, compression and laceration), and whiplash shaken infant syndrome.

As used herein, chronic neurodegenerative disorders included within the methods of the present invention include Alzheimer's disease, Pick's disease, diffuse Lewy body disease, progressive supranuclear palsy (Steel-Richardson syndrome), multisystem degeneration (Shy-Drager syndrome), chronic epileptic conditions associated with neurodegeneration, motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohifart-Kugelberg-Welander disease, spastic paraparesis, progressive multifocal leukoencephalopathy, familial dysautonomia (Riley-Day syndrome), and prion diseases (including, but not limited to Creutzfeldt-Jakob, Gerstmann-Straussler-Scheinker disease, Kuru and fatal familial insomnia).

As used herein, plexopathies include plexus palsies, multifocal neuropathies, sensory neuropathies, motor neuropathies, sensory-motor neuropathies, infections neuropathies, autonomic neuropathies, sensory-autonomic neuropathies, demyelinating neuropathies (including, but not limited to Guillain-Barre syndrome and chronic inflammatory demyelinating polyradiculoneuropathy), other inflammatory and immune neuropathies, neuropathies induced by drugs, neuropathies induced by pharmacological treatments, neuropathies induced by toxins, traumatic neuropathies (including, but not limited to compression, crush, laceration and segmentation neuropathies), metabolic neuropathies, endocrine and paraneoplastic neuropathies, and other neuropathies such as Charcot-Marie-Tooth disease (type 1a, 1b, 2, 4a, 1-X linked), Friedreich's ataxia, metachromatic leukodystrophy, Refsum's disease, adrenomyeloneuropathy, Ataxia-telangiectasia, Dejerine-Sottas neuropathy (types A and B), Lambert-Eaton syndrome, and disorders of the cranial nerves.

As used herein, unless otherwise noted, the term "halogen" shall include iodine, bromine, chlorine and fluorine.

As used herein, the term "alkyl" whether used alone or as part of a substituent group, include straight and branched chains comprising one to eight carbon atoms. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of one to four carbon atoms.

The term "alkenyl", whether used alone or as part of a substituent group, shall include straight and branched alkene chains comprising two to eight carbon atoms. Suitable examples include vinyl, 1-propenyl, 2-propenyl, 1-butenyl. 2-butenyl, 1-pentenyl, 2-pentenyl, 1-isobut-2-enyl, and the like. Similarly, the term "alkynyl", whether used alone or as part of a substituent group, shall include straight and branched alkyne chains comprising two to eight carbon atoms. Suitable examples include 2-propynyl, 2-butynyl, 1-butynyl, 1-pentynyl, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, the term "cycloalkyl" shall denote saturated monocyclic ring structures comprising three to eight ring carbons, preferably 5 to 7 carbons. Suitable examples include cyclopropyl, cyclobutyl, cyclopentyl, cyclohexyl, cycloheptyl and cyclooctyl.

As used herein, the term "aryl" indicates aromatic carbocyclic ring structures such as phenyl, naphthyl, and the like.

As used herein, unless otherwise noted, "aralkyl" shall mean any lower alkyl group substituted with an aryl group. For example, benzyl, phenylethyl, phenylpropyl, naphthylmethyl, and the like.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, isoxazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like. Preferred heteroaryl groups include pyridyl, thienyl and imidazolyl.

As used herein, the term "heterocycloalkyl" shall denote any five to seven membered monocyclic, saturated, partially unsaturated or partially aromatic ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any carbon atom of the ring such that the result is a stable structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

When a particular group is "substituted" (e.g., cycloalkyl, aryl, aralkyl, heteroaryl, heterocycloalkyl), that group may have one or more substituents, preferably from one to five substituents, more preferably from one to three substituents, most preferably from one to two substituents, independently selected from the list of substituents.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

Under standard nomenclature used throughout this disclosure, the terminal portion of the designated side chain is described first, followed by the adjacent functionality toward the point of attachment. Thus, for example, a "phenylC$_1$–C$_6$alkylaminocarbonylC$_1$–C$_6$alkyl" substituent refers to a group of the formula

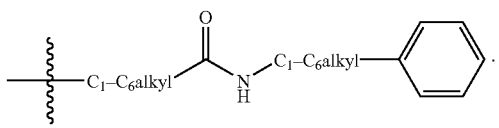

The term "subject" as used herein, refers to an animal, preferably a mammal, most preferably a human, who is or has been the object of treatment, observation or experiment.

As used herein, the term "composition" is intended to encompass a product comprising the specified ingredients in the specified amounts, as well as any product which results, directly or indirectly, from combinations of the specified ingredients in the specified amounts.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds of this invention include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Abbreviations used in the instant specification, particularly the Schemes and Examples, are as follows:

| | | |
|---|---|---|
| BHT | = | 2,6-bis-(t-butyl)-4-methyl-phenol |
| BSA | = | Bovine Serum Albumin |
| cAMP or cyclic AMP | = | Cyclic-adenosine monophosphate |
| DCE | = | 1,2-dichloroethane |
| DEAD | = | Diethyl azodicarboxylate |
| DM | = | Differentiation Medium |
| DMF | = | Dimethyl formamide |
| DMEM | = | Dulbeccos Minimal Essential Medium |
| DMSO | = | Dimethylsulfoxide |
| DPBS | = | Dulbeccos phosphate buffered saline |
| EDTA | = | Ethylene Diamine Tetraacetic Acid |
| FBS | = | Fetal bovine serum |
| GDP | = | Guanosine Diphosphate |
| GTP | = | Guanosine Triphosphate |
| GM | = | Growth Medium |
| HBSS | = | Hank's Buffered salt Solution |
| HEPES | = | 4-(2-Hydroxyethyl)-1-piperizine ethane sulfonic acid |
| HS | = | Human Serum |
| IgG | = | Immunoglobulin G |
| % Inh | = | Percent Inhibition |
| MEM | = | Minimum Essential Medium |
| NBS | = | N-bromosuccinimide |
| NCS | = | N-chlorosuccinimide |
| NDP αMSH | = | [Nle$^4$, D-Phe$^7$]αMSH, an analog of αMSH |
| PBS | = | Phosphate Buffered saline |
| PEG | = | Polyethylene Glycol |
| PNC | = | Penicillin |
| rt or RT | = | Room Temperature |
| SPA | = | Scintillation Proximity Assay |
| STM | = | Streptomycin |
| TLC | = | Thin layer chromatography |
| TM | = | Transition Medium |
| TMS | = | Trimethylsilyl |

Compounds of formula (I) wherein R$^3$ is hydrogen may be prepared according to the process outlined in Scheme 1.

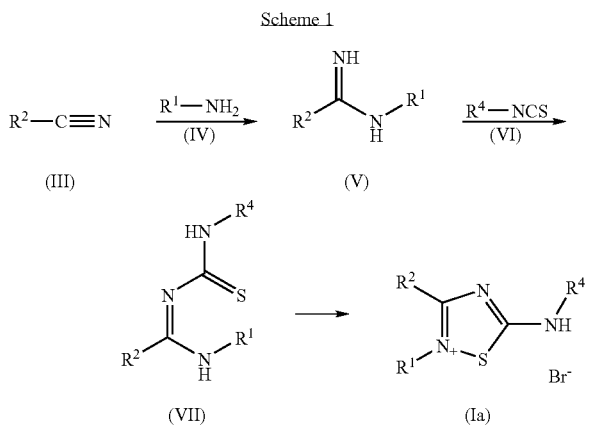

Scheme 1

More particularly, a suitably substituted cyano compound of formula (III), a known compound or compound prepared by known methods, is reacted with a suitably substituted primary amine of formula (IV), a known compound or compound prepared by known methods, in the presence of a base such as NaNH$_2$, NaH, NaN(TMS)$_2$, and the like, preferably NaNH$_2$, at an elevated temperature, preferably at about reflux, to yield the corresponding compound of formula (V).

The compound of formula (V) is reacted with a suitably substituted thiocyanate of formula (VI), a known compound or compound prepared by known methods, in the presence of DCE, at an elevated temperature, preferably about 45° C., to yield the corresponding compound of formula (VII).

The compound of formula (VII) is subjected to ring closure/oxidation, in the presence of Br$_2$, at room temperature, to yield the corresponding compound of formula (Ia).

Compounds of formula (II) may be prepared from suitably substituted compounds of formula (I) wherein R$^3$ is hydrogen according to the process outlined in Scheme 2.

Scheme 2

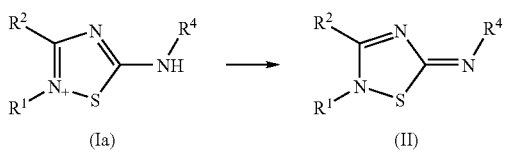

(Ia)                    (II)

More particularly, a suitably substituted compound of formula (Ia) is treated with a base such as NaHCO$_3$, Na$_2$CO$_3$, NaOH, and the like, preferably NaHCO$_3$, at room temperature, to yield the corresponding compound of formula (II).

Compounds of formula (II) may also be prepared from suitably substituted compounds of formula (VII) according to the process outlined in Scheme 3.

Scheme 3

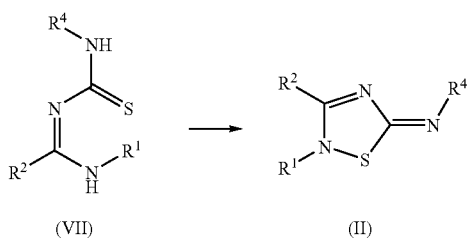

(VII)                    (II)

More particularly, a suitably substituted compound of formula (VII) is reacted with an oxidizing agent such as NBS, NCS, DEAD, and the like, preferably NBS, at room temperature, to yield the corresponding compound of formula (II). Preferably, the compound of formula (II) is extracted from a basic aqueous solution such as NaHCO$_3$, Na$_2$CO$_3$, NaOH, and the like.

Compounds of formula (I) wherein R$^3$ is alkyl may be prepared from a suitably substituted compound of formula (II) according to the process outlined in Scheme 4.

Scheme 4

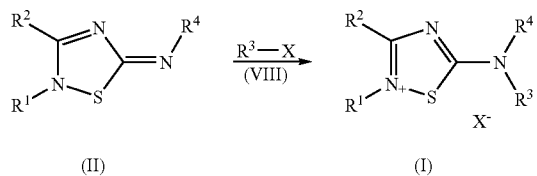

(II)                    (I)

Accordingly, a suitably substituted compound of formula (II) is reacted with a suitably substituted compound of formula (VIII), a known compound or compound prepared by known methods, wherein X$^-$ is trifluoromethylsulfonate, Br$^-$, and I$^-$, at room temperature, to yield the corresponding compound of formula (I).

Compounds of formula (I) wherein R$^3$ is hydrogen may be prepared from a suitably substituted compound of formula (II) according to the process outlined in Scheme 5.

Scheme 5

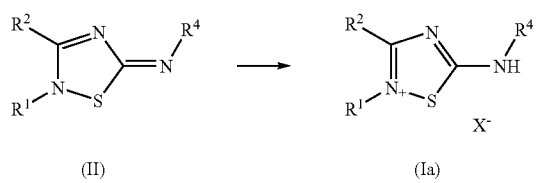

(II)                    (Ia)

Accordingly, a suitably substituted compound of formula (II) is reacted with a pharmaceutically acceptable acid such as HCl, HBr, HNO$_3$, and the like, preferably HCl, at room temperature, to yield the corresponding compound of formula (Ia), wherein X$^{-1}$ is Cl$^-$, Br$^-$, NO$_3^-$, and the like.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wliey & Sons, 1991. The protecting groups may be removed at a convenient subsequent stage using methods known from the art.

The utility of the compounds of the present invention to treat disorders mediated by a melanocortin receptor can be determined according to the procedures described in Examples 4–11 herein. The present invention therefore provides a method of treating such disorders, which comprises administering any of the compounds as defined herein in a quantity effective to treat the disorder (i.e. in a therapeutically effective amount). The compound may be administered to a patient afflicted with such a disorder by any conventional route of administration, including, but not limited to, intravenous, oral, subcutaneous, intramuscular, intradermal, parenteral and transdermal.

The present invention also provides pharmaceutical compositions comprising one or more compounds of this invention in association with a pharmaceutically acceptable carrier.

To prepare the pharmaceutical compositions of this invention, one or more compounds of formula (I) and/or (II) or a salt thereof (the active ingredient), is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

Topical formulations included within the present invention, include but are not limited to creams, lotions, multiple emulsions, microemulsions, liposomal creams or gels, gels, solutions, suspensions, ointments, foaming aerosols, hard or soft gelatin capsules, masks, sticks, roll-ons, powders, spray forms, and the like. The topical formulations may contain, in addition to the active ingredient(s), one or more non-active components including, but are not limited to chelating agents, buffering agents, colorants, preservatives, fragrances, emulsifiers, surfactants, opacifying agents, emollients, solvents, sunscreens, viscosity modifying agents, antioxidants, moisturizers, permeations enhancers, film formers, and the like.

Topical formulations for acne treatment included within the present invention may also contain one or more of the following components, including comedolytic/keratolytic agents, antimicrobial agents and steroidal or non-steroidal anti-inflammatory agents. (Comedolytic agents refer to any compound capable of rupturing a comedo. Keratolytic agents refer to any compound capable of breaking apart keratinocyes resulting in exfoliation of the epidermis.) Suitable comedolytic/keratolytic agents include, but are not limited to retinoids, salicylic acid, glycolic acid, cetyl betaine, and the like. Suitable antimicrobial agents include, but are not limited to benzoyl peroxide, erythromycin, tetracycline, clindamycin, azelaic acid, and the like. Topical formulations typically contain 0.01–1% active ingredient.

The pharmaceutical compositions herein will contain, per dosage unit, e.g., tablet, capsule, powder, injection, teaspoonful and the like, an amount of the active ingredient necessary to deliver an effective dose as described above. The non-topical pharmaceutical compositions herein will contain, per unit dosage unit, e.g., tablet, capsule, powder, injection, suppository, teaspoonful and the like, of from about 0.03 mg to 100 mg/kg (preferred 0.1–30 mg/kg) and may be given at a dosage of from about 0.1–300 mg/kg/day (preferred 1–50 mg/kg/day). The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders mediated by a melanocortin receptor described in the present invention may also be carried out using a pharmaceutical composition comprising any of the compounds as defined herein and a pharmaceutically acceptable carrier. The non-topical pharmaceutical composition may contain between about 0.01 mg and 100 mg, preferably about 5 to 50 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders mediated by a melanocortin receptor is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day. Preferably, the range is from about 0.03 to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended, and should not be construed to limit in any way the invention set forth in the claims which follow thereafter.

EXAMPLE 1

2-(2-methoxyphenyl)-3-phenyl-5-p-tolylamino-[1,2,4]thiadiazol-2-ium Compound #31

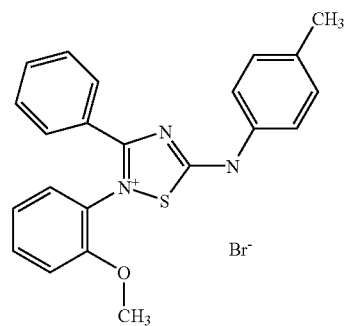

STEP A:

A mixture of o-anisidine (15.0 g, 121.8 mmol) and sodium amide (50 wt. % suspension in toluene) (11.40 g, 146.2 mmol) in anhydrous toluene (200 ml) was stirred for 1 hour at room temperature. To the mixture was added benzonitrile (9.86 ml, 96.6 mmol) and heated under reflux for 16 hours. The reaction mixture was cooled and 1.0N HCl (150 ml) was added to quench the reaction. Activated carbon was added and the reaction mixture was filtered through a Celite pad. The pH of the mixture was adjusted to about 14 by addition of 1.0 N NaOH (200 ml). The aqueous layer was extracted with chloroform (3×150 ml). The combined organic layer was dried over anhydrous MgSO$_4$, and evaporated. The resulting solid was washed with hexane and dried over the vacuum to yield the product as a pale white solid.

$^1$H NMR (300 MHz, CDCl$_3$) ™ 3.83 (s, 3H), 4.79 (s, 2H), 6.96(m, 3H), 7.04 (m, 1H), 7.43 (m, 3H), 7.93 (d, 2H)

MS (APCl, MH$^+$) 227

STEP B:

A mixture of N-arylbenzamidine (3.0 g, 13.27 mmol), prepared as in Step A, and 4-tolylisothiocyanate (2.18 g, 14.60) in anhydrous chloroform (30 ml) was heated under reflux for 16 hours. The reaction mixture was cooled and the solvent was evaporated. The resulting residue was purified by flash column chromatography with a mobile phase of 25% hexane in dichloromethane. The combined fractions were evaporated; and the resulting solid was dried over vacuum to yield the product as a yellow solid.

$^1$H NMR (300 MHz, CDCl$_3$) ™ 2.36 (s, 3H), 3.66 (s, 3H), 6.76 (m, 1H), 6.97 (t, 1H), 7.17–7.39 (m, 7H), 7.47 (d, 2H), 7.60 (d, 2H), 8.20 (s, 1H), 14.18 (s, 1H)

MS (ES, MH$^+$) 376.29

STEP C:

To the solution of thiourea (2.90 g, 7.73 mmol), prepared as in STEP B, in anhydrous chloroform (15 ml) was slowly added bromine (438 µl, 8.51 mmol). After stirring for 16 hours, the solvent was evaporated. The resulting solid was washed with anhydrous ethyl ether. The crude product was re-crystallized from 20% water in ethanol to yield the product as a yellow solid.

$^1$H NMR (300 MHz, CDCl$_3$) ™ 2.39 (s, 3H), 3.66 (s, 3H), 6.96 (d, 1H), 7.06 (t, 1H), 7.20–8.07 (m, 7H), 7.61 (d, 2H), 7.80 (d, 2H), 12.40 (s, 1H)

MS (ES, MH$^+$) 374.25

EXAMPLE 2

2-(2-methoxyphenyl)-3-(2-methoxyphenyl)-5-phenylamino-[1,2,4]thiadiazol-2-ium Compound #74

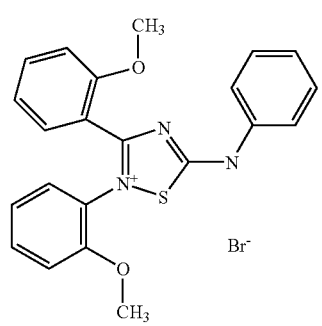

STEP A:

A mixture of o-anisidine (13.5 g, 110.0 mmol) and sodium amide (50 wt. % suspension in toluene) (9.40 g, 120.0 mmol) in anhydrous toluene (200 ml) was stirred for 1 hour at room temperature. To the mixture was added 2-methoxybenzonitrile (16 ml, 131.0 mmol) and the reaction mixture was then heated under reflux for 16 hours. The reaction mixture was cooled and 1.0N HCl (150 ml) was added to quench the reaction. Activated carbon was added and the reaction mixture was filtered through a Celite pad. The pH of the mixture was adjusted to about 14 by addition of 1.0 N NaOH (200 ml). The aqueous layer was extracted with chloroform (3×150 ml). The combined organic layer was dried over anhydrous MgSO$_4$, and evaporated. The resulting solid was washed with hexane and dried over the vacuum to yield the product as a pale white solid.

MS (APCl, MH$^+$) 257

STEP B:

A mixture of N-arylbenzamidine (15.5 g, 60.6 mmol), prepared as in STEP A and phenylisothiocyanate (8.70 mL, 72.7 mmol) in anhydrous chloroform (30 ml) was heated at 45° C. for 16 hours. The reaction mixture was cooled and the solvent was evaporated. The resulting residue was purified by flash column chromatography with a mobile phase of 25% hexane in dichloromethane. The combined fractions were evaporated and the resulting solid was dried over vacuum to yield the product as a yellow solid.

MS (ES, MH$^+$) 391.50

STEP C:

To a solution of thiourea (12.95 g, 33.1 mmol), prpeared as in STEP B, in anhydrous chloroform (15 ml) was slowly added bromine (1.78 mL, 34.75 mmol). After stirring for 16 hours, the solvent was evaporated. The resulting solid was washed with anhydrous ethyl ether. The crude product was re-crystallized from 20% water in ethanol to yield the product as a yellow solid.

MS (ES, MH$^+$) 390.1

Following the procedures disclosed herein, representative compounds of formula (I) of the present invention were prepared, as listed in Table 1.

TABLE 1

| ID No. | $R^1$ | $R^2$ | $R^3$ | $R^4$ |
|---|---|---|---|---|
| 1 | 4-methylphenyl | phenyl | H | 4-methoxyphenyl |
| 2 | 4-methylphenyl | phenyl | H | phenyl |
| 3 | 4-methylphenyl | phenyl | H | 2-methoxyphenyl |
| 4 | 4-methylphenyl | phenyl | H | 4-methylphenyl |
| 5 | 4-methylphenyl | phenyl | H | 2-methylphenyl |
| 6 | 4-methylphenyl | phenyl | H | 4-chlorophenyl |
| 7 | 4-methylphenyl | phenyl | H | 2-chlorophenyl |
| 8 | 2-methylphenyl | phenyl | H | phenyl |
| 9 | 2-methylphenyl | phenyl | H | 4-methoxyphenyl |
| 10 | 2-methylphenyl | phenyl | H | 2-methoxyphenyl |
| 11 | 2-methylphenyl | phenyl | H | 4-methylphenyl |
| 12 | 2-methylphenyl | phenyl | H | 2-methylphenyl |
| 13 | 2-methylphenyl | phenyl | H | 4-chlorophenyl |
| 14 | 2-methylphenyl | phenyl | H | 2-chlorophenyl |
| 15 | 4-chlorophenyl | phenyl | H | phenyl |
| 16 | 4-chlorophenyl | phenyl | H | 4-methoxyphenyl |
| 17 | 4-chlorophenyl | phenyl | H | 2-methoxyphenyl |
| 18 | 4-chlorophenyl | phenyl | H | 4-methylphenyl |
| 19 | 4-chlorophenyl | phenyl | H | 2-methylphenyl |
| 20 | 4-chlorophenyl | phenyl | H | 4-chlorophenyl |
| 21 | 4-chlorophenyl | phenyl | H | 2-chlorophenyl |
| 22 | phenyl | phenyl | H | phenyl |
| 23 | phenyl | phenyl | H | 4-methoxyphenyl |

TABLE 1-continued

R²-C(=N)-N(R⁴)-C(=N-R³)-S-N-R¹⁺ Br⁻ (1,2,4-thiadiazolium structure)

| ID No. | R¹ | R² | R³ | R⁴ |
|---|---|---|---|---|
| 24 | phenyl | phenyl | H | 2-methoxyphenyl |
| 25 | phenyl | phenyl | H | 4-methylphenyl |
| 26 | phenyl | phenyl | H | 2-methylphenyl |
| 27 | phenyl | phenyl | H | 4-chlorophenyl |
| 28 | 2-methoxyphenyl | phenyl | H | phenyl |
| 29 | 2-methoxyphenyl | phenyl | H | 4-methoxyphenyl |
| 30 | 2-methoxyphenyl | phenyl | H | 2-methoxyphenyl |
| 31 | 2-methoxyphenyl | phenyl | H | 4-methylphenyl |
| 32 | 2-methoxyphenyl | phenyl | H | 2-methylphenyl |
| 33 | 2-methoxyphenyl | phenyl | H | 4-chlorophenyl |
| 34 | 2-methoxyphenyl | phenyl | H | 2-chlorophenyl |
| 35 | 4-methoxyphenyl | phenyl | H | phenyl |
| 36 | 4-methoxyphenyl | phenyl | H | 4-methoxyphenyl |
| 37 | 4-methoxyphenyl | phenyl | H | 2-methoxyphenyl |
| 38 | 4-methoxyphenyl | phenyl | H | 4-methylphenyl |
| 39 | 4-methoxyphenyl | phenyl | H | 2-methylphenyl |
| 40 | 4-methoxyphenyl | phenyl | H | 4-chloro phenyl |
| 41 | 4-methoxyphenyl | phenyl | H | 2-chlorophenyl |
| 42 | 2-chlorophenyl | phenyl | H | phenyl |
| 43 | 2-chlorophenyl | phenyl | H | 4-methoxyphenyl |
| 44 | 2-chlorophenyl | phenyl | H | 2-methoxyphenyl |
| 45 | 2-chlorophenyl | phenyl | H | 4-methylphenyl |
| 46 | 2-chlorophenyl | phenyl | H | 2-methylphenyl |
| 47 | 2-chlorophenyl | phenyl | H | 4-chlorophenyl |
| 48 | 2-chlorophenyl | phenyl | H | 2-chlorophenyl |
| 49 | phenyl | phenyl | H | 2-chlorophenyl |
| 50 | 4-methylphenyl | phenyl | CH₃ | 4-methoxyphenyl |
| 51 | phenyl | phenyl | H | 4-methoxybenzyl |
| 52 | phenyl | phenyl | H | 2-methoxybenzyl |
| 53 | phenyl | phenyl | H | 4-methylbenzyl |
| 54 | phenyl | phenyl | H | 2-methylbenzyl |
| 55 | phenyl | phenyl | H | 4-chlorobenzyl |
| 56 | phenyl | phenyl | H | 2-chlorobenzyl |
| 57 | 4-methoxyphenyl | 4-methoxyphenyl | H | phenyl |
| 58 | 4-methoxyphenyl | 4-methoxyphenyl | H | 4-methoxyphenyl |
| 59 | 4-methoxyphenyl | 4-methoxyphenyl | H | 2-methoxyphenyl |
| 60 | 4-methoxyphenyl | 4-methoxyphenyl | H | 4-methylphenyl |
| 61 | 4-methoxyphenyl | 4-methoxyphenyl | H | 2-methylphenyl |
| 62 | 4-methoxyphenyl | 4-methoxyphenyl | H | 4-chlorophenyl |
| 63 | 4-methoxyphenyl | 4-methoxyphenyl | H | 2-chlorophenyl |
| 64 | 4-methoxyphenyl | 4-methoxyphenyl | H | 3-pyridyl |
| 65 | 2-methoxyphenyl | 4-methylphenyl | H | phenyl |
| 66 | 2-methoxyphenyl | 4-methylphenyl | H | 4-methoxyphenyl |
| 67 | 2-methoxyphenyl | 4-methylphenyl | H | 2-methoxyphenyl |
| 68 | 2-methoxyphenyl | 4-methylphenyl | H | 4-methylphenyl |
| 69 | 2-methoxyphenyl | 4-methylphenyl | H | 2-methylphenyl |
| 70 | 2-methoxyphenyl | 4-methylphenyl | H | 4-chlorophenyl |
| 71 | 2-methoxyphenyl | 4-methylphenyl | H | 2-chlorophenyl |
| 72 | 2-methoxyphenyl | 4-methylphenyl | H | 3-pyridyl |
| 73 | 2-methoxyphenyl | phenyl | H | 3-pyridyl |
| 74 | 2-methoxyphenyl | 2-methoxyphenyl | H | phenyl |
| 75 | 2-methoxyphenyl | 2-methoxyphenyl | H | 4-methoxyphenyl |
| 76 | 2-methoxyphenyl | 2-methoxyphenyl | H | 2-methoxyphenyl |
| 77 | 2-methoxyphenyl | 2-methoxyphenyl | H | 4-methylphenyl |
| 78 | 2-methoxyphenyl | 2-methoxyphenyl | H | 2-methylphenyl |
| 79 | 2-methoxyphenyl | 2-methoxyphenyl | H | 4-chlorophenyl |
| 80 | 2-methoxyphenyl | 2-methoxyphenyl | H | 2-chlorophenyl |
| 81 | 2-methoxyphenyl | 2-methoxyphenyl | H | 3-pyridyl |
| 84 | phenyl | phenyl | H | benzyl |
| 85 | 2-methoxyphenyl | 2-methoxyphenyl | H | 4-bromophenyl |
| 86 | 2-methoxyphenyl | 2-methoxyphenyl | H | 2,6-difluorophenyl |
| 87 | 2-methoxyphenyl | 2-methoxyphenyl | H | 2-chloro-6-methylphenyl |
| 88 | 2-methoxyphenyl | 2-methoxyphenyl | H | 3,5-difluorophenyl |

EXAMPLE 3

2-(2-methoxyphenyl)-3-(2-methoxyphenyl)-5-phenylamino-[1,2,4]-thiadiazole Compound #89

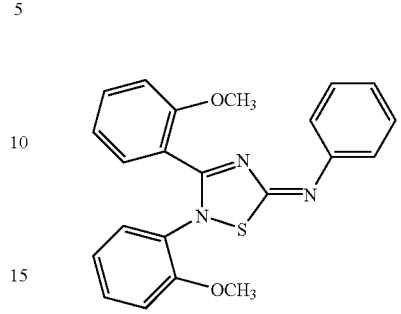

To a solution of the compound prepared as in Step B of Example 2 (0.921 g, 2.36 mmol) in anhydrous chloroform (10 mL) was added N-chlorosuccinimide (326 mg, 2.71 mmol). The reaction mixture was then stirred for 16 hours, and then stopped and washed twice with aqueous $NaHCO_3$. The organic layer was dried over magnesium sulfate and the remaining solvent removed under vacuum to yield the title product as a solid.

MS (ES, MH+) 390.1

Following the procedures described herein, representative compounds of formula (II) of the present invention were prepared, as listed in Table 2.

TABLE 2

| ID No. | R¹ | R² | R⁴ |
|---|---|---|---|
| 82 | 4-methylphenyl | phenyl | phenyl |
| 83 | 4-methylphenyl | phenyl | 4-methoxyphenyl |
| 89 | 2-methoxyphenyl | 2-methoxyphenyl | phenyl |
| 90 | 2-methoxyphenyl | 2-methoxyphenyl | 2,6-difluoro phenyl |
| 91 | 2-methoxyphenyl | 2-methoxyphenyl | 2-chloro-6-methylphenyl |
| 92 | 2-methoxyphenyl | 2-methoxyphenyl | 3,5-difluorophenyl |

Unless otherwise noted, NMR spectra, were measured on a Bruker Avance 300 MHz NMR spectrometer. Unless otherwise noted, molecular weights were measured using a Micromass LC platform electrospray mass spectrometer, as listed in Table 3.

TABLE 3

| ID No | MW 1 (as +ion) | MW 2 (w/Br–) | Meas. MW |
|---|---|---|---|
| 1 | 374.49 | 454.39 | 374.0 |
| 2 | 344.46 | 424.36 | 344.0 |
| 3 | 374.49 | 454.39 | 374.3 |
| 4 | 358.49 | 438.39 | 358.3 |
| 5 | 358.49 | 438.39 | 358.4 |
| 6 | 378.91 | 458.81 | 378.1, 380.3 |
| 7 | 378.91 | 458.81 | 378.2, 380.2 |
| 8 | 344.46 | 424.36 | 344.3 |
| 9 | 374.49 | 454.39 | 374.2 |
| 10 | 374.49 | 454.39 | 374.2 |
| 11 | 358.49 | 438.39 | 358.3 |
| 12 | 358.49 | 438.39 | 358.3 |
| 13 | 378.91 | 458.81 | 378.2, 380.2 |
| 14 | 378.91 | 458.81 | 378.2, 380.2 |

TABLE 3-continued

| ID No | MW 1 (as +ion) | MW 2 (w/Br−) | Meas. MW |
|---|---|---|---|
| 15 | 364.88 | 444.78 | 346.2, 366.2 |
| 16 | 394.90 | 474.81 | 394.1, 396.1 |
| 17 | 394.90 | 474.81 | 394.1, 396.1 |
| 18 | 378.91 | 458.81 | 378.2, 380.2 |
| 19 | 378.91 | 458.81 | 378.2, 380.2 |
| 20 | 399.32 | 479.23 | 398.1, 400.1 |
| 21 | 399.32 | 479.23 | 398.1, 400.0 |
| 22 | 330.43 | 410.34 | 330.3 |
| 23 | 360.46 | 440.37 | 360.3 |
| 24 | 360.46 | 440.37 | 360.3 |
| 25 | 344.46 | 424.37 | 344.4 |
| 26 | 344.46 | 424.37 | 344.3 |
| 27 | 364.88 | 444.78 | 364.2, 366.2 |
| 28 | 360.46 | 440.37 | 360.3 |
| 29 | 390.49 | 470.39 | 390.2 |
| 30 | 390.49 | 470.39 | 390.2 |
| 31 | 374.49 | 454.39 | 374.3 |
| 32 | 374.49 | 454.39 | 374.3 |
| 33 | 394.90 | 474.81 | 394.1, 396.1 |
| 34 | 394.90 | 474.81 | 394.1, 396.1 |
| 35 | 360.46 | 440.37 | 360.3 |
| 36 | 390.49 | 470.39 | 390.3 |
| 37 | 390.49 | 470.39 | 390.3 |
| 38 | 374.49 | 454.39 | 374.3 |
| 39 | 374.49 | 454.39 | 374.3 |
| 40 | 394.90 | 474.81 | 394.2, 396.2 |
| 41 | 394.90 | 474.81 | 394.2, 396.2 |
| 42 | 364.88 | 444.78 | 364.3, 366.3 |
| 43 | 394.90 | 474.81 | 394.2, 396.2 |
| 44 | 394.90 | 474.81 | 394.2, 396.2 |
| 45 | 378.91 | 458.81 | 378.2, 380.2 |
| 46 | 378.91 | 458.81 | 378.2, 380.2 |
| 47 | 399.32 | 479.23 | 398.1, 400.1 |
| 48 | 399.32 | 479.23 | 398.1, 400.1 |
| 49 | 364.88 | 444.78 | 364.2, 366.2 |
| 50 | 388.51 | 537.58 | 388.3 |
| 51 | 374.49 | 454.39 | 374.3 |
| 52 | 374.49 | 454.39 | 374.3 |
| 53 | 358.49 | 438.39 | 358.4 |
| 54 | 358.49 | 438.39 | 358.4 |
| 55 | 378.91 | 458.81 | 378.3, 380.3 |
| 56 | 378.91 | 458.81 | 378.3, 380.3 |
| 57 | 390.49 | 470.39 | 390.1 |
| 58 | 420.51 | 500.42 | 420.1 |
| 59 | 420.51 | 500.42 | 420.1 |
| 60 | 404.51 | 484.42 | 404.1 |
| 61 | 404.51 | 484.42 | 404.0 |
| 62 | 424.93 | 504.83 | 424.0, 426.0 |
| 63 | 424.93 | 504.83 | 424.0, 426.0 |
| 64 | 391.47 | 471.38 | 391.0 |
| 65 | 374.49 | 454.39 | 374.2 |
| 66 | 404.51 | 484.42 | 404.2 |
| 67 | 404.51 | 484.42 | 404.1 |
| 68 | 388.51 | 468.42 | 388.3 |
| 69 | 388.51 | 468.42 | 388.2 |
| 70 | 408.93 | 488.84 | 408.6, 410.0 |
| 71 | 408.93 | 488.84 | 408.1, 410.0 |
| 72 | 375.47 | 455.38 | 375.2 |
| 73 | 361.45 | 441.35 | 361. |
| 74 | 390.49 | 470.39 | 390.2 |
| 75 | 420.51 | 500.42 | 420.2 |
| 76 | 420.51 | 500.42 | 420.2 |
| 77 | 404.51 | 484.42 | 404.1 |
| 78 | 404.51 | 484.42 | 404.1 |
| 79 | 424.93 | 504.84 | 424.1, 426.1 |
| 80 | 424.93 | 504.84 | 424.1, 426.1 |
| 81 | 391.47 | 471.38 | 391.1 |
| 82 | 343.45 | | 344.3 |
| 83 | 373.48 | | 374.3 |
| 84 | 344.46 | 424.36 | 344.3 |
| 85 | 469.38 | 549.29 | |
| 86 | 426.5 | 506.4 | 426.3 |
| 87 | 439.0 | 518.9 | 438.3, 440.3 |
| 88 | 426.5 | 506.4 | 426.2 |
| 89 | 389.5 | | 390.1 |
| 90 | 425.5 | | 426.2 |
| 91 | 437.9 | | 438.3, 440.3 |
| 92 | 425.5 | | 426.2 |

EXAMPLE 4

Melanocortin MC-4 Receptor Binding Assay

Melanocortin [MC-4]-membrane [purchased from Receptor Biology Inc] was coupled to wheat germ agglutinin coated polyvinyl toluene-Scintillation Proximity Assay beads [purchased from Amersham Pharmacia Inc.] for 30 min at 25° C. Into each well of a 96-well Opti plate [purchased from Packard, Calif.], 2.5 µg of membrane and 0.25 mg of beads were mixed in a volume of 100 µL media. The media was 50 mM HEPES, pH 7.4 containing 0.1% bovine serum albumin, 2 mM $CaCl_2$, 2 mM $MgCl_2$ and protease inhibitors. Test compounds (1.5 µL) at 1 mM in 30% DMSO-50 mM HEPES, pH 7.4 buffer was added to separate wells on the plate. Radioactive ligand $^{125}$I-NDP-melanocyte stimulating hormone [NEN, 2000Ci/mmol] was added to each well (48.5 µL per well, 40 pM final concentration). The plate was then sealed and let stand for 16 hr at 25° C. NDP-Melanocyte stimulating hormone peptide and α-melanocyte stimulating hormone peptide [purchased from Palomar Research Inc, 1 µM] were used as reference inhibitor compounds to define non-specific binding (N). Total binding (T) was defined using 30% DMSO-50 mM HEPES, pH 7.4 buffer. Bound radioactivity for each well (Y), measured at counts per minute (cpm) was measured in a Top-Count [Packard, Calif.]. Percent inhibition was calculated as:

$$[(T-Y)/(T-N)]*100\%$$

EXAMPLE 5

Cyclic-Adenosine Monophosphate [cAMP] Stimulation Assay

Human Bowes melanoma cells expressing human melanocortin MC-4 receptor were grown to confluence in a 24-well culture plate. The growth medium was discarded and to each well was added 0.5 mL of Hank's solution. Test compounds were added to wells of a 96 well plate. NDP-melanocyte stimulating hormone peptide (1 µM) was added to the positive control wells while negative control wells received vehicle of 30% DMSO-50 mM HEPES, pH 7.4 buffer. The plate was incubated at 37° C. and 5% $CO_2$ for 30 min. The supernatant was discarded and the cells were washed twice with Hank's solution. Ethanol (80%, 0.5 mL) was added to each well and the plates were incubated at 4° C. for 30 min. Cyclic AMP content was measured using the NEN Flashplate kit [NEN]. A melanocortin receptor agonist is defined as a test compound which resulted in an increase in cAMP production in this assay.

EXAMPLE 6

G-protein Activation Assay

For each assay, membranes expressing the melanocortin MC-4 receptor (5 µg) were incubated for 5 min at 25° C.

with 0.5 nM $^{35}$S-GTPγS in 100 μL of 25 mM HEPES buffer, pH 7.5 containing 100 mM NaCl, protease inhibitors, 0.5 μM GDP, 5 mM 2-mercaptoethanol, 1 mM MgCl$_2$ together with test compound, 1 μM of NDP-melanocyte stimulating hormone or a combination of NDP-melanocyte stimulating hormone and test compound. Basal $^{35}$S-GTPγS binding was defined by 10 mM HEPES, pH 7.4 buffer containing 30% DMSO. The reaction was terminated by addition of 50 μl of termination buffer containing 25 mM HEPES, pH 7.5, 20 mM MgCl$_2$, protease inhibitors, 100 μM GDP, 100 μM GTP, 5 mM 2-mercaptoethanol with detergents (0.5% digitonin, 0.2% sodium deoxycholate, and 0.5% NP-40). The membranes were solubilized for 30 minutes at 25° C. The $^{35}$S-GTPγS bound Gαs protein was immunoprecipitated using anti-Gαs (0.5 μg) that linked to anti-rabbit IgG protein A conjugated SPA. Bound radioactivity was measured in a Topcount [Packard]. Non-specific $^{35}$S-GTPγS binding was defined by $^{35}$S-GTPγS immunoprecipitated by normal rabbit IgG (0.5 μg).

| | |
|---|---|
| Basal binding (B) | = Mean counts/minute (cpm) immunoprecipitated by anti- Gαs. |
| Non-specific binding (NSB) | = Mean cpm immunoprecipitated by normal rabbit IgG. |
| Specific basal binding (SB) | = B-NSB |
| Cpm in each well | = C |
| Net cpm in each well (N) | = C-NSB |
| % stimulation | = [(N-SB)/SB] × 100% |

The procedures described above for the melanocortin MC-4 receptor were repeated for the melanocortin MC-3 receptor. Following the procedures described, representative compounds of the present invention were tested for binding in the MC-4 and/or MC-3 assay, as listed in Table 4.

TABLE 4

| ID No. | IC$_{50}$ MC-4 (μM) (Filtration) | IC$_{50}$ MC-4 (nM) (SPA) |
|---|---|---|
| 1 | 1.1 | 174 |
| 2 | 1.5 | 234 |
| 3 | 0.7 | 159 |
| 4 | inactive | 297 |
| 5 | 1.3 | 207 |
| 6 | 2.5 | 293 |
| 7 | 2.2 | 218 |
| 8 | 1.4 | 201 |
| 9 | 1.1 | 217 |
| 10 | 2.3 | 130(90) |
| 11 | 2.4 | 243 |
| 12 | insoluble | insoluble |
| 13 | 3.4 | 347 |
| 14 | 5.6 | 234 |
| 15 | 4.5 | 482 |
| 16 | 4.3 | 424 |
| 17 | 7.7 | 351 |
| 18 | 6.0 | 463 |
| 19 | 3.9 | 460 |
| 20 | 3.5 | 636 |
| 21 | 7.8 | 392 |
| 22 | | 124 |
| 23 | | 124 |
| 24 | | 76 |
| 25 | | 57 |
| 26 | | 63 |
| 27 | | 89 |
| 28 | | 68 |
| 29 | | 48 |
| 30 | | 103 |
| 31 | | 22 |
| 32 | | 48 |
| 33 | | 91 |
| 34 | | 46 |
| 35 | | 100 |
| 36 | | 79 |
| 37 | | 72 |
| 38 | | 159 |
| 39 | | 146 |
| 40 | | 133 |
| 41 | | 483 |
| 42 | | 482 |
| 43 | | 237 |
| 44 | | 89 |
| 45 | | 246 |
| 46 | | 368 |
| 47 | | 874 |
| 48 | | 444 |
| 49 | | 96 |
| 50 | | 30,000 |
| 51 | | 1,000 |
| 52 | | 1,000 |
| 53 | | 1,000 |
| 54 | | 800 |
| 55 | | 800 |
| 56 | | 3,000 |
| 57 | | inactive |
| 58 | | inactive |
| 59 | | inactive |
| 60 | | inactive |
| 61 | | inactive |
| 62 | | inactive |
| 63 | | 1,000 |
| 64 | | 1,200 |
| 65 | | 114 |
| 66 | | 120 |
| 67 | | 130 |
| 68 | | 110 |
| 69 | | 139 |
| 70 | | 566 |
| 71 | | 234 |
| 72 | | 155 |
| 73 | | 725 |
| 74 | | 194 |
| 75 | | 103 |
| 76 | | 332 |
| 77 | | 4.4 |
| 78 | | 99 |
| 79 | | 216 |
| 80 | | 378 |
| 81 | | 672 |
| 82 | 1.5 | 826 |
| 83 | 1.9 | 833 |
| 84 | 82 nm | |
| 85 | | |

EXAMPLE 7

Rodent Feeding: Food Intake in Food-Deprived Rats (MC-4)

Male Long-Evans rats (180–200 grams) were housed individually and maintained on a once-a-day feeding schedule (i.e.10 a.m. until 4 p.m.) for five days following quarantine to allow the animals to acclimate to feeding on powdered chow (#5002 PMI Certified Rodent Meal) during the allotted time. The chow was made available in an open jar, anchored in the cage by a wire, with a metal follower covering the food to minimize spillage. Water was available ad-libitum.

Animals were fasted for 18 hours prior to testing. At the end of the fasting period, animals were administered either a test compound or vehicle. Vehicle and test compound were administered either orally (5 mL/kg) 60 minutes prior to the experiment, subcutaneously (1 mL/kg) 30 minutes prior to the experiment, or intraperitoneally (1 mL/kg) 30 minutes prior to the experiment. Test compounds were administered orally as a suspension in aqueous 0.5% methylcellulose-0.4% Tween 80, or intraperitoneally as a solution or suspension in PEG 200; compound concentrations typically ranged from 1 mg/kg to 100 mg/kg, preferably from 10–30 mg/kg. Food intake was measured at 2, 4, and 6 hours after administration by weighing the special jar containing the food before the experiment and at the specified times. Upon completion of the experiment, all animals were given a one-week washout period before re-testing.

Following the procedure described above, select compounds of the present invention were tested to measure the effect on food intake in fasted rats, as listed in Table 5 and 6.

TABLE 5

| ID No. | [mg/kg], Route | Food Intake 0–2 hrs | Food Intake 2–6 hrs |
|---|---|---|---|
| PEG-200 | ip | 8.25 g | 13.38 g |
| 1 | 10μ, ip | 7.29 g | 8.43 g |

TABLE 6

| ID No | [mg/kg], Route | Change in Food Intake 0–2 hrs (%) | Change in Food Intake 2–6 hrs (%) |
|---|---|---|---|
| MCT Control | po | 0 | 0 |
| PEG-200 | ip | 0 | 0 |
| 1 | 10, ip | −11.60% | −37.00% |
| 1 | 30, po | −21.2 | −6.7 |
| 84 | 10, ip | −7 | −24.5 |
| 84 | 10, ip | 3.9 | −17.8 |
| 84 | 30, po | −7 | 32 |
| 26 | 10, ip | −12.7 | −32.3 |
| 27 | 30, ip | −27.4 | −29.1 |
| 29 | 30, po | −26.3 | −3.7 |
| 29 | 10, ip | −62.3 | −70.7 |
| 31 | 3, ip | −37.8 | −50 |
| 31 | 1, ip | −20.6 | −71.2 |
| 31 | 30, po | −23.6 | 31.5 |
| 31 | 10, po | −10.1 | 39.7 |
| 31 | 3, po | −9 | 52.1 |
| 31 | 1, po | 1.2 | 19.5 |
| 32 | 10, ip | −29.6 | −60.2 |
| 32 | 30, po | −12.5 | −15 |
| 32 | 10, po | −20 | −1 |
| 32 | 3, po | −11.5 | 31.17 |
| 32 | 1, po | −13.8 | 26 |
| 34 | 10, ip | −38 | −72 |
| 34 | 30, po | −7.5 | 2 |
| 34 | 10, po | −1.3 | −6 |
| 49 | 30, ip | −20.6 | −21.2 |

EXAMPLE 8

Neurite Cell Outgrowth Assay

Cell Culture:

Dissociated hippocampal and cortical cell cultures were established from embryonic day 18 rat fetuses as described by Mattson, M. P., Barger, S. W., Begley, J, and Mark, R. J., *Methods Cell Biol.*, 1994, 46:087–216. Briefly, fetuses were removed via cesarean section from pregnant moms (Sprague-Dawley) and anesthetized with halothane according to the AVMA Panel on Euthanasia. Pups were decapitated and the brains were removed and placed in HEPES-buffered Hank's Balanced Salt solution (HBSS; Gibco). The hippocampi and cortices were dissected out and pooled according to tissue-type. Tissue was trypsinized for 15 min (1 mg/ml trypsin-HBSS; Worthington), rinsed with fresh HBSS, incubated in trypsin inhibitor (1 mg/ml; Sigma) for 5 min, rinsed again with fresh HBSS and then triturated in 1 ml fresh HBSS with a fire-polished glass pipette. Dissociated cells were seeded at 30,000 cells/well onto poly-D-lysine coated 96-well plates (Collaborative BioScience). Each well contained 100 μl of Eagle's Minimal Essential Media (MEM; Gibco) supplemented with 26 mM $NaHCO_3$ (Sigma), 56 mM glucose (Sigma), 15 mM KCl (Sigma), 1 mM sodium pyruvate (Sigma), 1.1 mM L-glutamine (Sigma), 10% (v/v) heat-inactivated fetal bovine serum (Hyclone), and 0.001% gentamicin sulfate (Sigma) (pH 7.4). Cells were allowed to attach for 24 h in a humidified 37° C. 5% $CO_2$ incubator before experimental treatment. The culture media was aspirated and exchanged with fresh media every 3 days.

Assay:

Twenty-four hours after plating, cultures were treated with vehicle (PBS+0.1% BSA), alpha-melanocyte stimulating hormone (α-MSH) or test compound (diluted in DPBS). Each treatment condition was run in quadruplicate. On the third day in culture, the media was aspirated off and replaced with fresh media and test compound. At one week in culture, the cells were fixed with 10% phosphate-buffered formalin for 15 min, then rinsed with DPBS (Sigma) and placed in blocking serum for 30 min (horse serum; 1:50 dilution in DPBS; Vector Labs). The cultures were rinsed again with DPBS and then incubated in primary antibody for 2 hr (microtubule-associated protein-2 (MAP-2) is a selective marker for dendritic processes; anti-mouse monoclonal (Chemicon); 1:1000 dilution of MAP-2 in antibody diluent (Zymed)). Negative control wells were incubated in antibody diluent alone. Background signal was determined by blank wells (cell-free) incubated with or without antibody. Cultures were rinsed again with DPBS and then placed in fluorescein for 1 hr (FITC; anti-mouse IgG; rat adsorbed; 1:50 dilution in DPBS; Vector Labs). Cultures were rinsed a final time with DPBS and the plates were then read on a Cytofluor 4000 fluorescence plate reader. Neurite outgrowth was expressed as percent change from control (vehicle).

Selected compounds of the instant invention were tested in the above assay with results as listed in Table 7. The data are expressed as percent change over the vehicle response. All compounds were screened at 50 nM. The abbreviation NA indicates no change/not active; the abbreviation ND indicates a compound not tested/response not determined.

TABLE 7

| | Neurite Outgrowth | |
|---|---|---|
| Comp # | Hippocampal Cells | Cortical Cells |
| Vehicle | 19% | 4% |
| 1 | 6% | NA |

TABLE 7-continued

| | Neurite Outgrowth | |
|---|---|---|
| Comp # | Hippocampal Cells | Cortical Cells |
| 2 | 18% | 18% |
| 3 | 17% | 23% |
| 4 | 20% | 21% |
| 5 | 28% | 9% |
| 6 | 23% | 24% |
| 7 | NA | 11% |
| 8 | NA | 12% |
| 9 | NA | NA |
| 10 | 7% | 11% |
| 11 | 9% | 10% |
| 12 | 28% | 20% |
| 13 | 29% | 32% |
| 14 | 30% | 19% |
| 15 | 18% | 31% |
| 16 | 8% | 18% |
| 17 | 8% | 17% |
| 18 | 17% | 17% |
| 19 | 22% | NA |
| 20 | 17% | NA |
| 21 | 27% | 2% |
| 22 | NA | 30% |
| 23 | 10% | 20% |
| 24 | 10% | 16% |
| 25 | NA | 23% |
| 26 | 16% | 47% |
| 27 | 17% | 52% |
| 28 | NA | 25% |
| 29 | NA | 8% |
| 30 | NA | NA |
| 31 | NA | 16% |
| 32 | NA | 6% |
| 33 | NA | 21% |
| 34 | NA | 22% |
| 35 | NA | 28% |
| 36 | NA | 16% |
| 37 | NA | 26% |
| 38 | NA | NA |
| 39 | NA | ND |
| 40 | 26% | NA |
| 41 | 36% | 5% |
| 42 | 26% | NA |
| 43 | 30% | 37% |
| 44 | 43% | 19% |
| 45 | 46% | 25% |
| 46 | 40% | 19% |
| 47 | 20% | 13% |
| 48 | NA | 19% |
| 49 | 16% | 51% |
| 50 | 46% | NA |
| 51 | 74% | 28% |
| 52 | 65% | NA |
| 53 | 67% | NA |
| 54 | 45% | NA |
| 55 | 19% | NA |
| 56 | 33% | NA |
| 57 | 9% | NA |
| 58 | 72% | 10% |
| 59 | 61% | 21% |
| 60 | 66% | 14% |
| 61 | 66% | 17% |
| 62 | 13% | 13% |
| 63 | 20% | 17% |
| 64 | 22% | 12% |
| 82 | 14% | 15% |
| 83 | 11% | 9% |
| 84 | ND | 17% |

The data above show that cultures treated with select compounds of the present invention resulted in a significant increase in neurite outgrowth as measured by MAP2-FITC immunofluorescence. A comparison between the test compounds and α-MSH indicates that many of the test compounds were superior to α-MSH in promoting neurite outgrowth at the concentration tested. In addition, several of the test compounds displayed selective effects on neurite outgrowth in hippocampal or cortical cells.

EXAMPLE 9

In vivo Facial Nerve Compression Model

The ability of test compound to provide neuro-protective or neuro-regenerative effects was investigated in a facial nerve compression model. Facial nerve motor axons arise exclusively from neurons within the pons in a well-defined nucleus. Facial nerve compression results in retrograde reactions proximal to the lesion site and Wallerian degeneration at its distal part, which causes diminished whisker movement on the lesioned side.

Male Long-Evans rats (150–180 g) were anesthetized with 3–5% isoflorane for induction and 2% for maintenance during the surgical procedures. The right facial nerve was exposed and compressed with forceps for 30 sec at its exit from the stylomastoid foramen. The left facial nerve was sham-operated and served as an internal control. Nerve compression causes paralysis of whisker muscles, hence the reduced whisker movement on the lesioned side, which is observed immediately after recovery from anesthesia. The following morphological abnormalities associated with the functional deficit were observed:

(1) an increase in the number of perineuronal glial cells in the facial nucleus of the lesioned side, with the increased observed to peak around D3–6;

(2) a thinner myelin sheath and less myelin basic protein staining in the compressed facial nerve approximately one week after the lesion;

(3) morphological alterations around the N-M junction and whisker follicles regions and gradually degeneration of motor neurons in the facial nuclei.

After recovery from anesthesia, the rats were randomly divided into groups for dosing with vehicle, αMSH or test compound, with 6 animals per group. αMSH (s.c., 70 ug/each 48 hr) was used as a positive control. Test compounds were dosed p.o. at 20 mg/kg bid for 14 days. Restoration of whisker movement was monitored daily after the operation using two criteria:

(1) frequency of whisker movement on the lesioned side relative to the the opposite side (sham-operated) which served as the baseline control (2) semi-quantitative measurements (0 to 4+) on strength of the whisker muscles, characterized based on observation of the percentage of moved whiskers, muscle tone of whisker muscles, and the position of the nose. For all observations, the experimental design was blind to the behavioral observer.

The results of behavioral assessment showed that both test compounds, compounds #31 and #84, accelerated the recovery time to restore whisker muscle movement in the lesioned rats as compared to the vehicle controls (p<0.05). The recovery rate of the whisker movement was expressed as percentage of its own internal control (sham-operated), as listed in Table 8.

TABLE 8

Functional Recovery of Whisker Movement after Oral Administration of Compound #31 and #84 in Facial Nerve Compression Model

| | Percent Recovery | | | | | |
|---|---|---|---|---|---|---|
| | D9 | D10 | D11 | D12 | D13 | D14 |
| Unlesioned Site | 100 | 100 | 100 | 100 | 100 | 100 |
| Vehicle | 0 | 5.0 ± 6.8 | 27.6 ± 15.9 | 72.5 ± 21.2 | 86.4 ± 14.5 | 91.3 ± 8.3 |
| α-MSH | 2.0 ± 2.8 | 24.6 ± 15.8 | 60.1 ± 19.3 | 93.8 ± 14.0 | 98.1 ± 5.3 | 100 ± 0.0 |
| Cmpd #31 (246377) | 0 | 3.5 ± 3.1 | 67.8 ± 9.5 | 98.5 ± 3.7 | 100 ± 0.0 | 100 ± 0.0 |
| Cmpd #84 (153791) | 0 | 4.8 ± 4.3 | 35.1 ± 12.9 | 90.0 ± 10.9 | 98.3 ± 4.1 | 100 ± 0.0 |

EXAMPLE 10 in Vitro Assay: Measurement of Regulation of Sebaceous Lipid Synthesis

STEP A: Preparation of a Feeder Layer

Semiconfluent cultures of 3T3 mouse fibroblasts (Swiss Albino mouse, ATCC CCL-92) were treated with mitomycin C (4 μg/ml) for 3 hours, trypsinized and seeded at a density of $2.5 \times 10^5 / 9.5$ cm² tissue culture plate in Dulbeccos Minimal Essential Medium (DMEM) containing 10% Colorado Calf Serum, PNC (100U/ml), STM (100 μg/ml), L glutamine (0.3 mg/ml), sodium pyruvate (1 mM) and nonessential amino acids (100 μM). The cells were incubated at 37° C. for 24 hours prior to their use as a feeder layer for sebocytes.

STEP B: Isolation of Human Sebocytes

Human sebocytes were isolated from Dermatome shavings of postoperative pieces of human skin at 0.4–0.8 mm depths (this part of the skin was previously shown to be enriched in sebaceous glands). Shavings so obtained were treated with 1% Dispase in Iscoves medium containing 10% serum for 20 min at 37° C. The tissue was then placed in 0.3% trypsin/1% EDTA in Phosphate Buffered Saline (PBS) for 10 minutes at 37° C. Following this incubation the cells were gently scraped from the tissue in Growth medium (GM) containing DMEM/F12 media mixture (3:1), supplemented with 8% heat inactivated FBS, 2% heat inactivated human serum (HS), 1 mM sodium pyruvate, epidermal growth factor (10 ng/ml), insulin (10 μg/ml), hydrocortisone (0.4 μg/ml) and +/−cholera toxin (100 μg/ml), L-glutamine and antibiotics. Cells so obtained were filtered through nylon mesh (100% pore size), centrifuged at 750 RPM, re-suspended in GM and counted.

STEP C: Cultures of Human Sebocytes

Resultant cells from the above isolation procedure were plated on the 3T3 feeder layers at $2 \times 10^5 / 9.5$ cm² in growth medium and maintained at 37° C. and 5% $CO_2$ for 3 days (Phase I). Following the initial growth period they were transferred to a transition medium (TM) that consisted of DMEM/F12 media supplemented with 1 mM sodium pyruvate, insulin (10 g/ml), transferrin (6.7 ng/ml) and selenium (5.5 μg/ml) (ITS), 2% heat inactivated FBS and 2% heat inactivated human serum as well as +/−cholera toxin (ch.t.) (100 μg/ml), L-glutamine and antibiotics (Phase II). Three days later the cells were changed to differentiation medium (DM), DMEM/F12 supplemented with ITS, 3,3',5-triido-L-thyronine sodium (3 nM), 1%(v/v) trace element mix and the choice of differentiation agent i.e. bovine pituitary extract (10 μg/ml). This medium was changed every 3 days (Phase III).

STEP D: Testing Stimulators or Inhibitors of Sebocyte Differentiation and Lipid Production Hormones, mixture of hormones i.e. bovine pituitary extract or compounds to be tested were added to the culture at the beginning of phase III. Two criteria were used to evaluate the effect of these materials on sebaceous cultures: 1) visual observations and 2) evaluation of sebaceous lipid accumulation and synthesis. The evaluation of lipid accumulation completed using the Nile red method. This method relies on visualization of neutral lipids by Nile red and quantitation by reading of fluorescence at 535 nm excitation, 580 nm emission using a plate reader. The lipid synthesis was evaluated by radioactive labeling using $^{14}C$ acetate and quantified by Bio Rad Phosphoimager (Molecular Imager, FX) using 4.1 Software.

STEP E: Visual Observations & Nile Red Evaluation of Lipid Accumulation

Morphological evaluation of lipid accumulation was easily recognized since the cells enlarged and displayed lipid granules that in bright field light microscopy appeared as yellowish circles in the cells. Quantitation of accumulation/inhibition of neutral lipids in sebocytes was accomplished by Nile red binding assay. Briefly, following exposure of sebocytes to test compounds, the cells were allowed to interact with 1 μM Nile red in Hanks buffered saline solution containing DMSO and Pluronic F127. After 4 hours of incubation, washing and incubation overnight, the fluorescence was read at 535 excitation and 580 emission using a fluorescence plate reader. To determine whether the compounds had an inhibitory effect on cell growth, cell counts were performed.

Following the procedure described above, select compounds of the present invention were tested for visual and Nile red evaluation of lipid accumulation, with results as listed in Table 9.

TABLE 9

| ID No. | % Inh 0.4 μM | % Inh 0.8 μM | Visual* 0.4 μM | Visual* 0.8 μM | MC5-R $IC_{50}$ |
|---|---|---|---|---|---|
| 74 | 72 | 100 | +++ | ++++ | 154 nM |
| 76 | 48 | 88 | ++ | +++ | 317 nM |
| 80 | 61 | 91 | ++ | ++++ | 138 nM |
| 67 | N.T. | N.T. | ++ | +++ | 246 nM |

TABLE 9-continued

| ID No. | % Inh 0.4 µM | % Inh 0.8 µM | Visual* 0.4 µM | Visual* 0.8 µM | MC5-R IC$_{50}$ |
|---|---|---|---|---|---|
| 50 | 0 | 0 | 0 | 0 | No binding |
| 84 | 0 | 0 | 0 | 0 | No binding |

*Increased number of + signs indicates the degree of inhibition with ++++ = 100%, +++ = 75%, ++ =50% and + = 25% inhibition of lipid granule formation.

STEP F: Evaluation of Sebaceous Lipid Synthesis by Sebaceous Cells

At day 11 of the culture, sebocytes were labeled with $^{14}C$ acetate at a final concentration of 2 µCi/ml for 24 hours in serum free culture medium. The cells were than scraped from plates and frozen at −80° C. in glass vials. Lipid extraction was completed using the Bligh-Dyer method (Bligh, E. G. and Dyer, W. J., Can. J. Biochem. Physiol., 1959, 37, pp 911–916) with slight modification as detailed herein. Briefly, cells were homogenized in a 2:1 chloroform-methanol mixture, in the presence of KCl. The organic phase was removed from the mixture, the separated lipids were dried under argon and spotted to high performance thin layer chromatography (HPTLC) plates. The plates were developed by three separate mobile phases. The first was hexane (to the top of the plate), followed by toluene (to the top) and finally a 70:30:1 mixture of hexane:ether:acetic acid (half way up the plate-10 cm). The plates were than exposed to radiographic film for visualization of radioactive lipid species. For visualization of unlabeled lipids the plates were sprayed with 8% cupric acid and charred on a hot plate. Quantitation of the results was done by Image Pro Plus 3.0 (Media Cybernetics, Silver Springs, Md.).

Following the procedure described above, select compounds of the present invention were tested for their inhibitory effect on differentiation of human sebocytes. Visually, the stained cell cultures treated with compound #74 showed complete disappearance of lipid granules in sebocyte cultures following a seven day treatment. The same cells examined for lipid synthesis revealed inhibition of squalene, cholesterol esters and wax esters, as measured by radioactively labeled lipids separated by HPTLC. The cell panels were quantified by measurement of the intensity of bands using Image Pro Plus (version 5.0). % inhibition was calculated based on the difference between treated samples and vehicle treated controls, with results as listed in Table 10.

TABLE 10

| Lipid | Inducer | Cell Sex | % Inh @ 0.4 µM | % Inh @ 0.6 µM |
|---|---|---|---|---|
| Squalene | Cholera toxin & Bovine pituitary extract | F/M | 100/100 | 100/100 |
| Cholesterol ester | Cholera toxin & Bovine pituitary extract | F/M | 85/64 | 88/76 |
| Unknown | Cholera toxin & Bovine pituitary extract | F/M | 75/68 | 85/80 |
| Wax ester | Cholera toxin & Bovine pituitary extract | F/M | 70/50 | 67/42 |
| Triglyceride | Cholera toxin & Bovine pituitary extract | F/M | 0 | 0 |

EXAMPLE 11

In Vivo Evaluation of the Test Compound Effect on Sebum Production: Human Skin —SCID Mouse Chimera Model Severe combined immunodeficient mice (SCID) provide an invaluable model for skin xenografting. These animals are devoid of both T and B cell immunity. Human skin grafts in SCID mice retain human cellular tissue components including skin immune cells, i.e. Langerhans cells, macrophages and lymphocytes and also part of the engrafted endothelium (Kaufman R., et al., Exp. Dermatol. 1993: 2: 209–216, 1993). These properties allow for the study of physiological and/or pathological responses of human skin cells to a test compound.

STEP A: Method of Transplantation:

C.B-17 scid/scid mice (Taconic, Germantown, N.Y.) were used for grafting at 5–6 weeks of age. Full thickness human facial skin was shaved to ~0.4 mm using a Forman Dermatome. The skin shavings were washed 3 times in antibiotics and antimycotics (penicillin, streptomycin, fungizone) (Life technologies) in Dulbecco's Modified Eagle Medium (DMEM, Life Technologies). Eliptical skin ~2.0–2.5×1.0–1.5 was grafted onto the prepared graft bed and sutured using 4.0 silk. During surgical procedures the mice were anaesthetized using a mixture of Ketaset (0.16 mg/g body weight) and Rompun (8.0 µg/g body weight).

It is well accepted that the wound healing process of the transplanted skin in the SCID mouse takes one month, at which time the human skin can be used for experimental purposes. We also found that there is a gradual regeneration of sebaceous glands in the transplanted human skin and that these glands are fully regenerated and secrete sebum at 7 weeks as shown by Sebutape and histo-morphometry. Maximum size of the glands was observed 3 month post transplantation. The glands retained their capability to produce human specific sebum and the glandular tissue expressed human specific markers including MC5-R. Since glands reached their maximum size at 2–3 month post transplantation the effects of inhibitors of sebum secretion was tested at this point.

STEP B: Method of Treatment:

Mice at 2–3 month post transplantation with human facial skin were used for the studies. The graft area was treated with the test compound at the desired concentration(s) dissolved in polyethylene glycol-ethanol (20 µl/2 cm$^2$). Controls were treated with vehicle alone. The test compounds were applied daily, excluding weekends. Sebum secretion was determined using Sebutape at 15 days and 30 days following treatment.

STEP C: Termination of the Experiment:

The termination of the experiment was determined by preliminary clinical evaluation of sebum production using SEBUTAPE. At this time human skin grafts were excised and representative samples were collected for histological evaluation. More particularly, 2 mm punch biopsies were prepared and used for evaluation of lipid synthesis and total lipid accumulation in the treated tissues.

STEP D: Evaluation of Lipid Synthesis and Total Lipid Accumulation in the Examined Tissues.

The collected 2 mm punch biopsies were placed individually into 96 well plates in Krebs buffer and labeled with 10 µCi of $^{14}C$ acetate for 3 hours. Following this labeling period the samples were washed in medium and 5 biopsies pooled, weighed, and used for lipid extraction. The lipid extraction and analysis by HPTLC was the same as described for tissue culture derived cells.

Following the procedure described above, compound #74 of the present invention was tested for the inhibition of sebaceous gland activity following 11 day treatment of human skin transplanted to the SCID mouse.

Visual evaluation of the sebaceous gland following topical treatment with 0.1% solution of compound #74 resulted in visible shrinkage of the sebaceous gland and down regulation of sebaceous lipids. Topical treatment for 15 days with 0.05% and 0.005% solutions was not sufficient to down regulate the lipids. Numerical evaluation of the inhibition of human sebaceous lipids for these cells was analyzed using HPTLC, with results as listed in Table 11, 12 and 13. %Inhibition numbers are listed relative to control.

TABLE 11

Effect of Compound #74 on Human Sebaceous Lipids (11 Day Treatment)

| Lipid | % Inh @ 0.1% | % Inh @ 0.5% | % Inh @ 0.01% |
|---|---|---|---|
| Squalene | 70 | 0 | 0 |
| W/E | 80 | 10 | 25 |
| Triglycerides | 50 | 0 | 0 |

TABLE 12

Effect of Compound #74 on Lipid Accumulation (30 Day Treatment)

| Lipid | % Inh @ 0.05% | % Inh @ 0.01% |
|---|---|---|
| Squaline | 73 | 82 |
| Cholesterol Ester | 21 | 44 |
| Wax Esters | 93 | 86 |
| Triglycerides | 90 | 75 |
| Cholesterol | 82 | 33 |

TABLE 13

Effect of Compound #74 on Sebaceous Lipid Synthesis (30 Day Treatment)

| Lipid | % Inh @ 0.05% | % Inh @ 0.01% |
|---|---|---|
| Squaline | 90 | 80 |
| Wax Esters | 93 | 86 |
| Triglycerides | 90 | 75 |
| Cholesterol | 82 | 33 |

As shown in Tables 12 and 13 above, both total sebaceous lipid accumulation and de novo synthesis of sebaceous lipids was significantly decreased following 30 days of topical treatment with an 0.05% and 0.01% solution of compound #74.

EXAMPLE 12

Oral Formulation

As a specific embodiment of an oral composition, 100 mg of the compound #74 of Example 2 is formulated with sufficient finely divided lactose to provide a total amount of 580 to 590 mg to fill a size O hard gel capsule.

EXAMPLE 13

Topical Formulations

A: Microemulsion

As a specific embodiment of a microemulsion composition the following components are blended, with heating as need:

| | |
|---|---|
| Polysorbate 60 (e.g Tween 60 from ICI Surfactants) | 20 parts |
| Isopropyl Palmitate | 20 parts |
| Sorbitan Oleate (e.g. Span 80 from ICI Surfactants) | 13 parts |
| 2-Ethylhexanediol-1,3 | 4 parts |
| Butylated hydroxy-toluene | 0.05 parts |
| Compound #74 | 0.05 parts |

To the blended mixture is then slowly added water (42.9 parts by weight), with mixing as necessary, to yield the emulsion.

B: Hydroalcoholic Gel

As a specific embodiment of a hydroalcoholic gel composition the polypropylene glycol (10 parts by weight), butylene glycol (10 parts by weight), benzyl alcohol (2 parts by weight), EDTA (0.05 parts by weight) and BHT (0.05 parts by weight) are mixed with water (74.85 parts by weight total). The mixture is blended until all the components are dissolved. Carbomer (e.g. Carbopol 934P from Goodrich) (3 parts by weight) is then slowly added with constant turning to yield a gel. Compound #74 (0.05 parts by weight) is then dispersed into the gel with mixing. The gel pH is adjusted to about pH 3–4.

C: Anhydrous Gel

As a specific embodiment of an anhydrous gel isopropanol (20 parts by weight) is added to butylene glycol (20 parts by weight). BHT (0.05 parts by weight) and benzyl alcohol (1.0 parts by weight) are then added to the isopropanol/butylene glycol mixture. To the resulting mixture is then added Cyclotetrasiloxane ($D_4$) and Organopolysiloxane-11 (e.g. Gransil GSM Gel from Grant Industries) (58.85 parts by weight) with continuous mixing. Compound #74 (0.1 parts by weight) is micronized by and dispersed into the gel with continuous mixing until uniformly distributed.

D: Cream

As a specific embodiment of an o/w (oil/water) cream, the following components are mixed in the amounts (parts by weight) as noted. The final mixture is adjusted to about pH 2 with hydrochloric acid.

| | |
|---|---|
| Cetearyl alcohol | 4.3 parts |
| Microcrystalline wax | 9.0 parts |
| Ceteth-20 Surfactant (e.g. Brij 58 from ICI Surfactants)) | 1.1 parts |
| Capric/Caprylic Triglycerides (e.g. Tegosoft CT from GoldSchmidt) | 3.6 parts |
| Glycine | 0.6 parts |
| Compound #74 | 0.1 parts |
| BHT | 0.05 parts |
| Water | 81.25 parts |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the formula (II)

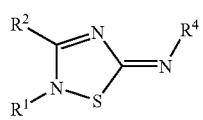

wherein
R¹ is substituted aryt;
wherein the substituted aryl is substituted with one or more substituents independently selected from halogen, hydroxy, alkyl, alkoxy; halogenated alkyl, halogenated alkoxy, amino, alkylamino or di(alkyl)amino;
R² is substituted aryl;
wherein the substituted aryl is substituted with one or more substituents independently selected from halogen, hydroxy, alkyl, alkoxy, trihalomethyl, trihalomethoxy, amino, alkylamino or di(alkyl)amino;
R⁴ is aryl; wherein the aryl is optionally substituted with one or more substituents independently selected from halogen, hydroxy, alkyl, alkoxy; halogenated alkyl, halogenated alkoxy, amino, alkylamino or di(alkyl) amino;
and pharmaceutically acceptable salts thereof.

2. A compound as in claim 1 wherein
R¹ is substituted aryl; wherein the aryl group is optionally substituted with one to two substituents selected from halogen, alkyl and alkoxy; R² is substituted aryl; wherein the aryl group is substituted with one to two substituents selected from alkyl and alkoxy;
R⁴ is selected from the group consisting of aryl and substituted aryl; wherein the substituents on the aryl are one to two independently selected from halogen, alkyl and alkoxy;
and pharmaceutically acceptable salts thereof.

3. A compound as In claim 2 wherein
R¹ is 2-methoxyphenyl;
R² is 2-methoxyphenyl;
R⁴ is selected from the group consisting of phenyl, 4-methoxyphenyl, 2,6-difluorophenyl, 3,5-difluorophenyl and 2-chloro-8-methylphenyl;
and pharmaceutically acceptable salts thereof.

4. A compound as in claim 3 selected from the group consisting of [2-(2-methoxyphenyl)-3-(2-methoxyphenyl)-2H-[1,2,4]-thiadiazol-5-ylidene]-phenylamine and pharmaceutically acceptable salts thereof.

5. A compound of the formula (II)

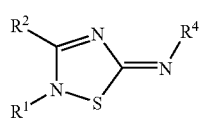

wherein
R¹ is substituted aryl;
wherein the substituted aryl is substituted with one or more substituents independently selected from halogen, hydroxy, alkyl, alkoxy halogenated alkyl, halogenated alkoxy, amino, alkylamino or di(alkyl)amino;
R² is aryl;
wherein the aryl, is substituted with one or more substituents independently selected from halogen, hydroxy, alkyl, alkoxy; trihalomethyl, trihalomethoxy, amino, alkylamino or di(alkyl)amino;
R⁴ is substituted aryl;
wherein the substituted aryl is substituted with one or more substituents independently selected from halogen, hydroxy, alkyl, alkoxy; halogenated alkyl, halogenated alkoxy, amino, alkylamino or di(alkyl)amino;
and pharmaceutically acceptable salts thereof.

6. A pharmaceutical composition comprising a compound as claimed in claim 1 and a pharmaceutically acceptable carrier.

7. A method of making a pharmaceutical composition comprising mixing a compound of claim 1 with a pharmaceutically acceptable carrier.

8. A pharmaceutical composition made by mixing a compound of claim 1 and a pharmaceutically acceptable carrier.

9. A pharmaceutical composition comprising a compound as claimed in claim 5 and a pharmaceutically acceptable carrier.

10. A method of making a pharmaceutical composition comprising mixing a compound of claim 5 with a pharmaceutically acceptable carrier.

11. A pharmaceutical composition made by mixing a compound of claim 5 and a pharmaceutically acceptable carrier.

12. A pharmaceutical composition comprising the compound of claim 2 and a pharmaceutically acceptable carrier.

13. A pharmaceutical composition comprising the compound of claim 3 and a pharmaceutically acceptable carrier.

14. The pharmaceutical composition of claim 7 wherein the pharmaceutical composition is a topical formulation.

15. The pharmaceutical composition of claim 12 wherein the pharmaceutical composition is a topical formulation.

16. The pharmaceutical composition of claim 13 wherein the pharmaceutical composition is a topical formulation.

17. The pharmaceutical composition of claim 14 wherein the topical formulation additionally contains one or more of the following components comedolytic/keratolytic agents, antimicrobial agents, steroidal anti-inflammatory agents and non-steroidal anti-inflammatory agents.

18. The pharmaceutical composition of claim 17 wherein the comedolytic/keratolytic agent is selected from the group consisting of retinoids, salicyclic acid, glycolic acid and cetyl betaine.

19. The pharmaceutical composition of claim 18 wherein the antimicrobial agents is selected from the group consisting of benzoyl peroxide, erythromycin, tetracycline, clindamycin and azelaic acid.

* * * * *